US011557390B2

(12) United States Patent
Hibbard

(10) Patent No.: US 11,557,390 B2
(45) Date of Patent: Jan. 17, 2023

(54) RADIOTHERAPY TREATMENT PLAN MODELING USING GENERATIVE ADVERSARIAL NETWORKS

(71) Applicant: Elekta, Inc., Atlanta, GA (US)

(72) Inventor: Lyndon Stanley Hibbard, St. Louis, MO (US)

(73) Assignee: Elekta, Inc., Atlanta, GA (US)

( * ) Notice: Subject to any disclaimer, the term of this patent is extended or adjusted under 35 U.S.C. 154(b) by 1274 days.

(21) Appl. No.: 15/966,228

(22) Filed: Apr. 30, 2018

(65) Prior Publication Data

US 2019/0333623 A1 Oct. 31, 2019

(51) Int. Cl.
*G16H 20/40* (2018.01)
*G06N 3/08* (2006.01)
*A61N 5/10* (2006.01)

(52) U.S. Cl.
CPC .......... *G16H 20/40* (2018.01); *A61N 5/1031* (2013.01); *A61N 5/1039* (2013.01); *G06N 3/08* (2013.01);
(Continued)

(58) Field of Classification Search
CPC .......... G16H 20/40; G06N 3/088; G06N 3/08; A61N 5/1031; A61N 2005/1041; A61N 5/1039; A61N 5/1038
See application file for complete search history.

(56) References Cited

U.S. PATENT DOCUMENTS

| 11,077,320 B1 | 8/2021 | Hibbard |
| 2013/0142310 A1 | 6/2013 | Fahimian et al. |

(Continued)

FOREIGN PATENT DOCUMENTS

| AU | 2019262835 | 3/2022 |
| CN | 106803082 | 6/2017 |

(Continued)

OTHER PUBLICATIONS

"International Application Serial No. PCT US2019 028720, International Search Report dated Oct. 16, 2019", 4 pgs.

(Continued)

*Primary Examiner* — Christine H Matthews
*Assistant Examiner* — Joshua Daryl D Lannu
(74) *Attorney, Agent, or Firm* — Schwegman Lundberg & Woessner, P.A.

(57) ABSTRACT

Techniques for generating radiotherapy treatment plans and establishing machine learning models for the generation and optimization of radiotherapy dose data are disclosed. An example method for generating a radiotherapy dose distribution using a generative model, trained in a generative adversarial network, includes: receiving anatomical data of a human subject that indicates a mapping of an anatomical area for radiotherapy treatment; generating radiotherapy dose data corresponding to the mapping with use of the trained generative model, as the generative model processes the anatomical data as an input and provides the dose data as output; and identifying the radiotherapy dose distribution for the radiotherapy treatment of the human subject based on the dose data. Another example method for training of the generative model includes establishing values of the generative model and a discriminative model of the generative adversarial network using adversarial training, including in a conditional generative adversarial network arrangement.

41 Claims, 10 Drawing Sheets

(52) U.S. Cl.
CPC ...... *G06N 3/088* (2013.01); *A61N 2005/1041* (2013.01)

(56) References Cited

U.S. PATENT DOCUMENTS

| | | | |
|---|---|---|---|
| 2017/0177812 | A1 | 6/2017 | Sjolund |
| 2018/0101770 | A1 | 4/2018 | Tanaka et al. |
| 2018/0144465 | A1* | 5/2018 | Hsieh ........................ G06N 3/04 |
| 2019/0318474 | A1* | 10/2019 | Han ........................ A61N 5/103 |
| 2021/0244971 | A1 | 8/2021 | Hibbard |
| 2021/0308487 | A1 | 10/2021 | Hibbard |

FOREIGN PATENT DOCUMENTS

| | | |
|---|---|---|
| CN | 107072624 | 8/2017 |
| CN | 107358626 | 11/2017 |
| CN | 107441637 | 12/2017 |
| CN | 107451619 | 12/2017 |
| CN | 112041026 | 12/2020 |
| JP | 2011147593 | 8/2011 |
| JP | 2017522097 | 8/2017 |
| JP | 2018063504 | 4/2018 |
| JP | 2019526380 | 9/2019 |
| WO | 2018048575 | 3/2018 |
| WO | 2019212804 | 11/2019 |
| WO | 2021159143 | 8/2021 |

OTHER PUBLICATIONS

"International Application Serial No. PCT US2019 028720, Written Opinion dated Oct. 16, 2019", 8 pgs.
Chris, McIntosh, "Fully automated treatment planning for head and neck radiotherapy using a voxel-based dose prediction and dose mimicking method", Physics in Medicine and Biology, vol. 62, No. 15, XP055416743, (Sep. 2, 2016), 5926-5944.
Rafid, Mahmood, "Automated Treatment Planning in Radiation Therapy using Generative Adversarial Networks", Arxiv.Org, Cornell University Library, 201 Olin Library Cornell University Ithaca, NY 14853, XP081113459, (Jul. 17, 2018), 15 pgs.
"Conditional Generative Adversarial Nets in TensorFlow", Agustinus Kristiadi's Blog, [Online]. Retrieved from the Internet: <URL: https://wiseodd.github.io/techblog/2016/12/24/conditional-gan-tensorflow/ >, 6 pgs.
Abadi, Martín, et al., "Tensorflow: Large-scale machine learning on heterogeneous distributed systems", arXiv preprint arXiv:1603.04467, (2016), 19 pgs.
Appenzoller, Lindsey M., et al., "Predicting dose-volume histograms for organs-at-risk in IMRT planning", Medical physics 39.12, (2012), 7446-7461.
Bishop, Christopher M., "Pattern Recognition and Machine Learning", Springer-Verlag New York, (2006), 758 pgs.
Breedveld, Sebastiaan, et al., "The equivalence of multi-criteria methods for radiotherapy plan optimization", Physics in Medicine & Biology 54.23, (2009), 7199-7209.
Creswell, Antonia, et al., "Generative Adversarial Networks: An Overview", IEEE Signal Processing Magazine 35.1, (2018), 53-65.
Goodfellow, Ian, et al., "Deep learning", vol. 1. Cambridge: MIT press, (2016), 802 pgs.
Goodfellow, Ian, et al., "Generative adversarial nets", Advances in neural information processing systems, (2014), 9 pgs.
Goodfellow, Ian, "NIPS 2016 tutorial: Generative adversarial networks", arXiv preprint arXiv:1701.00160, (2016), 57 pgs.
Hastie, Trevor, et al., "The elements of statistical learning: data mining, inference, and prediction", Springer series in statistics, (2001), 764 pgs.
He, Kaiming, et al., "Identity mappings in deep residual networks", European Conference on Computer Vision. Springer, Cham, (2016), 15 pgs.
Hesse, Christopher, "Image-to-Image Translation in Tensorflow Make discriminators do your work for you", [Online]. Retrieved from the Internet: <URL: https://affinelayer.com/pix2pix/>, (Jan. 25, 2017), 12 pgs.

Isola, Phillip, et al., "Image-to-image translation with conditional adversarial networks", arXiv preprint, (2016), 16 pgs.
Krizhevsky, Alex, et al., "Imagenet classification with deep convolutional neural networks", Advances in neural information processing systems, (2012), 9 pgs.
Lecun, Yann, et al., "Deep learning", nature 521.7553, (2015), 436-444.
Mirza, Mehdi, et al., "Conditional generative adversarial nets", arXiv preprint arXiv:1411.1784, (2014), 7 pgs.
Nguyen, Dan, et al., "Dose Prediction with U-net: A Feasibility Study for Predicting Dose Distributions from Contours using Deep Learning on Prostate IMRT Patients", arXiv preprint arXiv:1709.09233, (2017), 17 pgs.
Romeijn, Edwin H, et al., "A unifying framework for multi-criteria fluence map optimization models", Phys. Med. Biol. 49 (2004), (May 4, 2004), pp. 1991-2013.
Ronneberger, Olaf, et al., "U-net: Convolutional networks for biomedical image segmentation", International Conference on Medical image computing and computer-assisted intervention. Springer, Cham, (2015), 8 pgs.
Tseng, Huan-Hsin, et al., "Deep reinforcement learning for automated radiation adaptation in lung cancer", Medical physics 44.12, (2017), 6690-6705.
Wu, Binbin, et al., "Patient geometry-driven information retrieval for IMRT treatment plan quality control", Medical physics 36.12, (2009), 5497-5505.
Zarepisheh, Masoud, et al., "A DVH-guided IMRT optimization algorithm for automatic treatment planning and adaptive radiotherapy replanning", Medical physics 41.6Part1, (2014), 061711-1-061711-14.
Zhu, Xiaofeng, et al., "A planning quality evaluation tool for prostate adaptive IMRT based on machine learning", Medical physics 38.2, (2011), 719-726.
"International Application Serial No. PCT US2019 028720, International Preliminary Report on Patentability dated Nov. 12, 2020", 8 pgs.
U.S. Appl. No. 16/784,919 U.S. Pat. No. 11,077,320, filed Feb. 7, 2020, Adversarial Prediction of Radiotherapy Treatment Plans.
U.S. Appl. No. 17/304,500, filed Jun. 22, 2021, Adversarial Prediction of Radiotherapy Treatment Plans.
"Australian Application Serial No. 2019262835, First Examination Report dated Sep. 28, 2021", 3 pages.
"Japanese Application Serial No. 2020-560895, Notification of Reasons for Refusal dated Jan. 18, 2022", w English translation, 12 pgs.
"European Application Serial No. 19727774.2, Response to Communication under Rule 71(3) filed Jan. 12, 2022", Claims not amended in response filed, 3 pgs.
"Australian Application Serial No. 2019262835, Response filed Jan. 31, 2022 to First Examination Report dated Sep. 28, 2021", 1 pg.
"Chinese Application Serial No. 201980029131.3, Office Action dated Feb. 28, 2022", w English translation, 25 pgs.
"U.S. Appl. No. 16/784,919, Notice of Allowance dated Apr. 15, 2021", 10 pgs.
"U.S. Appl. No. 16/784,919, Corrected Notice of Allowability dated May 19, 2021", 4 pgs.
"International Application Serial No. PCT US2021 070119, International Search Report dated May 19, 2021", 5 pgs.
"International Application Serial No. PCT US2021 070119, Written Opinion dated May 19, 2021", 6 pgs.
"European Application Serial No. 19727774.2, Response to Communication pursuant to Rules 161(1) and 162 EPC filed Jun. 18, 2021", 32 pgs.
"U.S. Appl. No. 16/784,919, Corrected Notice of Allowability dated Jun. 30, 2021", 4 pgs.
Hibbard, Lyndon, "Adversarial Prediction of Radiotherapy Treatment Machine Parameters", Advances in Intelligent Data Analysis XIX; [Lecture Notes in Computer Science; Lect.Notes Computer], Springer InternationalPublishing, Cham,, (Oct. 1, 2020), 85-94.
"Ray Tracing (graphics)", Wikipedia https: en.wikipedia.org wiki Ray_tracing_(graphics), (2019), 15 pgs.
"Beam's Eye View", Wikipedia https: en.wikipedia.org wiki Beam%27s_eye_view, (Accessed on Mar. 13, 2020), 1 pg.

(56) References Cited

OTHER PUBLICATIONS

Babier, A, "Knowledge-based automated planning with three-dimensional generative adversarial networks", Medical Physics, (Dec. 21, 2018), 15 pgs.

Glassner, A S, "An Introduction to Ray Tracing", Morgan-Kauffman Part 1 out of 2, (1989), 177 pgs.

Glassner, A S, "An Introduction to Ray Tracing", Morgan-Kauffman Part 2 out of 2, (1989), 176 pgs.

Johnson, Hans J, "The ITK Software Guide", (Jul. 25, 2019), 997 pgs.

Kak, A C, "Principles of Computerized Tomographic Imagining Chapter 1", SIAM Philadelphia, (2001), 4 pgs.

Kak, A C, "Principles of Computerized Tomographic Imagining Chapter 2", SIAM Philadelphia, (2001), 43 pgs.

Kak, A C, "Principles of Computerized Tomographic Imagining Chapter 3", SIAM Philadephia, (2001), 64 pgs.

Kak, A C, "Principles of Computerized Tomographic Imagining Chapter 4", SIAM Philadelphia, (2001), 63 pgs.

Kak, A C, "Principles of Computerized Tomographic Imagining Chapter 5", SIAM Philadelphia, (2001), 25 pgs.

Kak, A C, "Principles of Computerized Tomographic Imagining Chapter 6", SIAM Philadelphia, (2001), 71 pgs.

Kak, A C, "Principles of Computerized Tomographic Imagining Chapter 7", SIAM Philadelphia, (2001), 22 pgs.

Kak, A C, "Principles of Computerized Tomographic Imagining Chapter 8", SIAM Philapelphia, (2001), 26 pgs.

Kak, A C, "Principles of Computerized Tomographic Imagining Index", SIAM Philadelphia, (2001), 6 pgs.

Kak, A C, "Principles of Computerized Tomographic Imagining Introduction", Siam Philadelphia, (2001), 9 pgs.

McIntosh, C, "Contextual Atlas Regression Forests: Multiple-Atlas-Based Automated Dose Prediction in Radiation Therapy", IEEE Transactions on Medical Imaging, 15 pgs.

Murphy, Kevin P, "Machine Learning a Probabilistic Perspective", MIT Press, Cambridge, MA, USA Part 2 out of 2, (2012), 549 pgs.

Nguyen, D, "A feasibility study for predicting optimal radiation therapy dose distributions of prostate cancer patients from patient anatomy using deep learning", Scientific Reports www.nature.com scientificreports, (Jan. 31, 2019), 10 pgs.

Rit, S, "The Reconstruction Toolkit (RTK), an open-source cone-beam CT reconstruction toolkit based on the Insight Toolkit (ITK)", 5 pgs.

Shirashi, S, "Knowledge-based prediction of three-dimensional dose distributions for external beam radiotherapy", Medical Physics, 43(1), (2015), 378-287.

Shirley, P, "Fundamentals of Computer Graphics", Chapter 10 Ray Tracing AK Peters, (2005), 785 pgs.

Wachowicz, K, "On the direct acquisition of beam's-eye-view images in MRI for integration with external beam radiotherapy", Physics in Medicine, 11 pgs.

Zhu, Jun-Yan, "Unpaired Image-to-Image Translation using Cycle-Consistent Adversarial Networks", IEEE International Conference on Computer Vision, (2017), 10 pgs.

"Japanese Application Serial No. 2020-560895, Response filed Apr. 8, 2022 to Notification of Reasons for Refusal dated Jan. 18, 2022", w English Claims, 57 pgs.

"Chinese Application Serial No. 201980029131.3, Response filed Jul. 15, 2022 to Office Action dated Feb. 28, 2022", w English Claims, 23 pgs.

\* cited by examiner

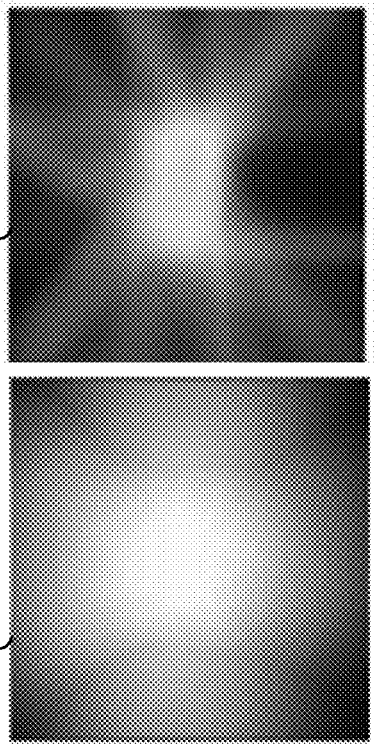
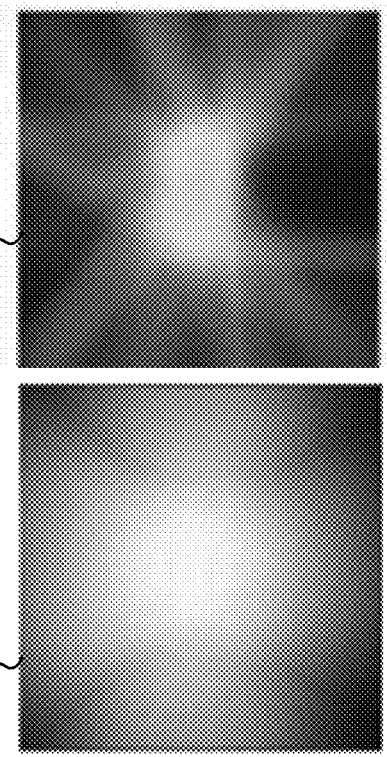
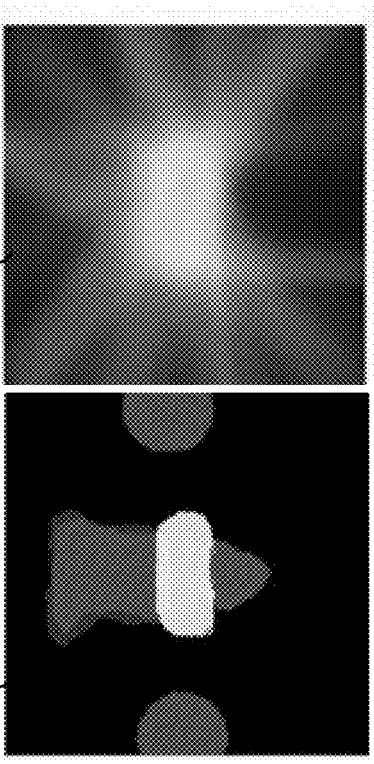
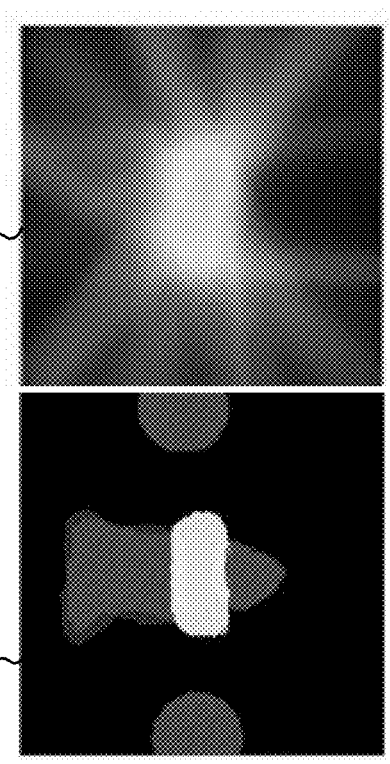
FIG. 8

RADIOTHERAPY TREATMENT PLAN MODELING USING GENERATIVE ADVERSARIAL NETWORKS

TECHNICAL FIELD

Embodiments of the present disclosure pertain generally to medical data and artificial intelligence processing techniques. In particular, the present disclosure pertains to the generation and use of data models in generative adversarial networks adapted for use with radiotherapy treatment planning workflows and system operations.

BACKGROUND

Intensity modulated radiotherapy (IMRT) and volumetric modulated arc therapy (VMAT) have become the standards of care in modern cancer radiation therapy. Treatment planning for these and other forms of radiotherapy involves customizing the particular exposure to radiation to the particular patient being treated, as critical organs are identified and target volumes are identified for treatment. Many approaches for creating individual patient IMRT or VMAT treatment plans involve a human-determined trial-and-error process, as an evaluator performs weighing target dose versus organ sparing tradeoffs, and as the evaluator adjusts program constraints whose effects on the dose distribution are very difficult to anticipate. In fact, the order in which the planning constraints are adjusted can itself result in dose differences. As a result, even skilled planners will often have no assurance that custom-designed radiotherapy plans are close to the best possible, to reach the objective of maximizing radiation treatment at the target volume while minimizing exposure to radiation in surrounding organs and tissue. Thus, planners are currently unable to determine whether a small or large amount of additional effort would lead to an improvement in the therapy plan.

Prior research has investigated whether radiotherapy plans are effective using two general approaches. First, research has evaluated plan quality that is associated with one-dimensional target-organ overlap measures (e.g., dose volume histograms (DVHs), overlap volume histograms (OVHs)), enabling comparison of such overlap measures with those of known high-quality plans in a database, to find and compare therapy plans. Second, research has also explored plan quality space to determine optimal, or even Pareto-optimal, families of plans that an operator may select for use in treatment. However, neither of these approaches provides or generates a detailed model of treatment planning independent of either planning process. As a result, the viability and success of a particular radiotherapy treatment is often reliant on manual human judgment that is available and exercised in the planning stage. Further, the reliance on human skill in the planning process (and the comparison with previous human-created therapy plans) prevents an objective determination of whether a new treatment plan is fully optimized for a particular patient and accomplishes the best possible treatment objectives.

Overview

The present disclosure includes procedures to develop, train, and utilize radiotherapy treatment plans using artificial intelligence (AI) processing techniques, including generative adversarial networks (GANs), deep neural networks (DNNs), and other forms of machine learning (ML) implementations. The present disclosure specifically includes a number of illustrative examples relevant to the use of discriminator and generator models, operating within a GAN, to learn a model of treatment planning for a particular cancer treatment that predicts a voxel-wise, 3D dose distribution customized to a particular patient's anatomy. These examples further involve use of the GAN models within learning, training, testing, and validation phases, as part of the radiotherapy treatment workflows used for planning and deploying radiotherapy treatment doses. However, it will be apparent that the presently described use and analysis of imaging data, dose data, and other radiotherapy-related information as part of a GAN (and other disclosed AI and ML techniques) may be incorporated into other medical workflows used for a variety of diagnostic, evaluative, interpretative, or treatment settings.

In an example, an implementation of a method for generating a radiotherapy dose distribution, as part of prediction or use of a GAN-trained artificial neural network model, comprises operations including: receiving anatomical data of a human subject, that indicates a mapping of an anatomical area for radiotherapy treatment of the human subject; generating, using a generative model, radiotherapy dose data corresponding to the mapping, with the generative model being trained in a generative adversarial network, using a generative model that is further trained to process the anatomical data as an input and provide the radiotherapy dose data as an output; and identifying the radiotherapy dose distribution for the radiotherapy treatment of the human subject based on the radiotherapy dose data.

Further examples of generating a radiotherapy dose distribution may include a deployment of a generative adversarial network that is configured to improve the generative model using a discriminative model, such that values applied by the generative model and the discriminative model are established using adversarial training between the discriminative model and the generative model. In further examples, the generative adversarial network is a conditional generative adversarial network comprising the generative model and a discriminative model, such that predicted values provided from the generative model are conditioned on the imaging data captured from the human subject. Further, the generative model and the discriminative model may be conditioned on pre-classified anatomical structure data during training, or conditioned on at least one constraint associated with the radiotherapy dose distribution.

Also in an example, an implementation of a method for producing a trained model for generating a radiotherapy dose distribution may include: establishing values of a generative model and a discriminative model of the generative adversarial network using adversarial training; adapting the adversarial training to include training the generative model to generate a simulated radiotherapy dose distribution image from an input image, and training the discriminative model to classify a generated radiotherapy dose distribution image as simulated or real training data, such that the output of the generative model is used for training the discriminative model, and the output of the discriminative model is used for training the generative model; and outputting the generative model for use in generating radiotherapy treatment dose information, as the generative model is adapted for identifying a radiotherapy dose data for a radiotherapy treatment of a human subject based on input anatomical data that corresponds to a mapping of an anatomical structure for the radiotherapy treatment.

Further examples of producing the trained model may include use of a conditional generative adversarial network, including conditioning the generative model and the discriminative model during training using pre-defined anatomical structure data. In various examples, the generative model may be trained to generate the radiotherapy dose data for a particular condition or anatomical feature based on image data, or on a plurality of anatomical areas for respective radiotherapy treatments. Additional constraints, conditions, inputs, and other variations may also be provided in connection with training or use of the trained model.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIG. 8 illustrates variations of pairs of anatomical area information and output dose representations provided in a treatment dose model.

DETAILED DESCRIPTION

Figure 1:
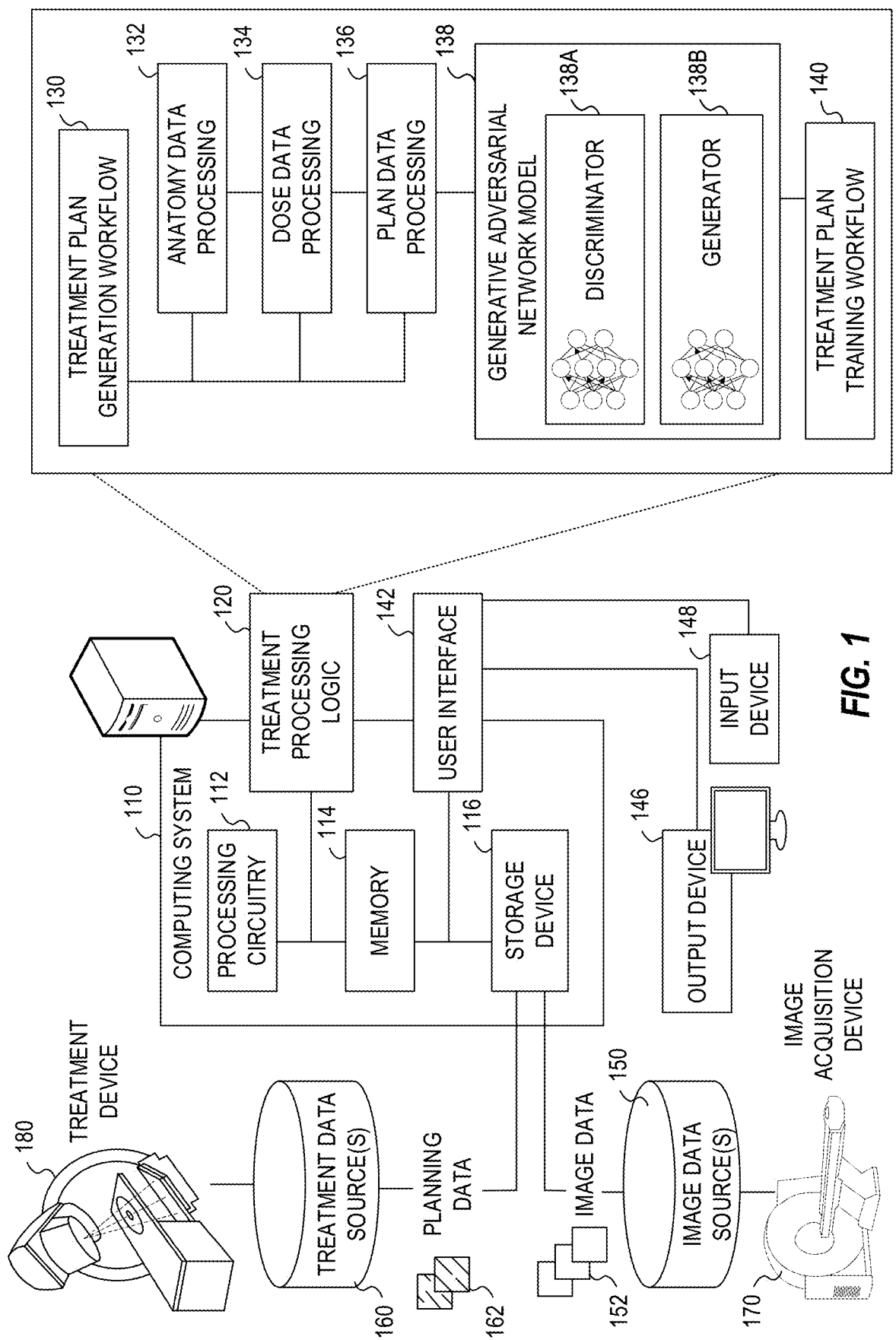
FIG. 1 illustrates an exemplary radiotherapy system adapted for performing treatment plan generation processing.

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

The present disclosure includes various techniques to improve the operation of radiotherapy treatment planning and data processing, including in a manner that provides technical advantages over manual (e.g., human-directed, -assisted or -guided) and conventional approaches for developing or deploying radiotherapy treatment plans. These technical advantages include reduced computing processing times to generate plan data, improved efficiency in data analysis operations, reproducibility and refined improvement of later developed treatment plan data and data values, and accompanying improvements in processing, memory, and network resources used to conduct radiotherapy treatment planning and operational workflow activities. These improved planning and workflow activities may be applicable to a variety of medical treatment and diagnostic settings and the information technology systems used in such settings, in addition to the improvement in data management, visualization, and control systems that manage data to support such treatment and diagnostic actions. Accordingly, in addition to these technical benefits, the present techniques may also result in many apparent medical treatment benefits (including improved accuracy of radiotherapy treatment, reduced exposure to unintended radiation, and the like).

As further discussed herein, the following uses and deployments of a generative adversarial network (GAN), a form of supervised artificial intelligence (AI) machine learning, enable an improvement in the accuracy and usefulness of a radiotherapy treatment plan through a learned model. In an example, the present techniques output a projected treatment plan that can indicate an accurate projection of a radiotherapy dose for a new patient, as determined from and customized to the patient's specific anatomy indicated by imaging data. The learned models discussed herein may also enable uses within a system that can be used to check the quality of existing treatment plans, initiate a custom treatment plan, and assist planning or verification at many different stages of radiotherapy treatment. Further, the learned models may aid in automated planning, which is important in the use of adaptive radiotherapy protocols where repeated planning and adjustments are used. The use of the present learned models and automated approaches thus can provide significant benefit for medical facilities that lack deep local expertise or resources (and thus lack the ability or skills for a manual treatment planning process to be performed).

In an example, the learned models are produced using a pair of deep neural networks operating in a GAN: a generator (also referred to as a "generative model") that produces estimates of the probability distribution describing the training data; and a discriminator (also referred to as a "discriminative model") that classifies generator samples as belonging to the generator or to the training data. The generator aims to emulate the data distribution of the training data as completely as possible, and thereby maximally confuse the discriminator. As a result, a generator is produced that is trained (in essence, "tuned") to maximize the results of regression in predictive modeling.

In an example, the GAN is trained on a model of treatment planning for a particular radiotherapy treatment, to train the model to generate a voxel-wise, 3D dose distribution given an anatomical input (e.g., a particular patient's anatomy). The model is learned by submitting pairs of registered anatomy and dose data (e.g., 2D or 3D images, or other spatial-based anatomy and dose data representations) to the GAN models and validated by testing the resulting model with anatomy/dose image pairs not used in the training. In further examples, testing procedures may be used to verify that the trained generative model is producing useful results. Such procedures may include reconstructing the test dose images in 3D, and evaluating dose volume histograms (DVHs) of the planning treatment volumes (PTVs) and organs at risk (OARs) compared to DVHs derived from the known treatment plans comprising the training data.

The use of a GAN two-network (generator-discriminator) architecture may be used to produce a trained generative model that predicts treatment dose estimates which are superior to previous implementations and DNN architectures, including prior approaches of supervised ML in neural networks. Additionally, the use of a conditional GAN with the present techniques may provide additional improvements for improved training towards specific anatomical areas and features and the specific type of treatment and treatment constraints experienced by the patient or the type of radiotherapy treatment. These and a variety of other technological and functional benefits will be apparent from the following sections.

The approaches discussed herein enable the discovery of the properties of radiotherapy treatment plans and dosage for many variations of diagnosis and treatment prescription, to predict the likely dose distribution based on the distributions of patient anatomies, planning parameters, and constraints learned in this data. These approaches use a kind of statistical learning employed by GANs to obtain a much more detailed model of the linkages between patient anatomies and constraints, and a more accurate dose prediction relative to earlier deep learning approaches.

By employing this powerful machine learning method, the present approaches may produce a model of a treatment plan process, encapsulating the many subjective decisions made during plan creation, to produce plans that could be used directly, or to produce plans that form templates (starting points) for subsequent planning, or to predict which existing plans are likely to perform poorly, or to provide assistance for treatment clinics lacking deep local expertise, or even to automate treatment planning itself. This is particularly appealing in view of the increasing use of adaptive therapy in which repeated planning is required.

Conventional approaches have only explored basic uses of deep learning networks, including GAN implementations, for data processing actions such as modeling lung cancer radiotherapy protocols and estimating the efficacy of dose escalation. However, such analyses are not based on a pixel-wise imaging model, and do not use a pixel-wise learning approach. Further, prior approaches have not explored ways of improving the operation and accuracy of a GAN, such as with the use of conditional GAN (e.g., conditioned on image data or radiotherapy operational constraints).

FIG. 1 illustrates an exemplary radiotherapy system adapted to perform radiotherapy plan processing operations using one or more of the approaches discussed herein. These radiotherapy plan processing operations are performed to enable the radiotherapy system to provide radiation therapy to a patient based on specific aspects of captured medical imaging data and therapy dose calculations. Specifically, the following processing operations may be implemented as part of a treatment plan generation workflow 130 and a treatment plan training workflow 140, implemented by treatment processing logic 120. It will be understood, however, that many variations and use cases of the following trained models and treatment processing logic 120 may be provided, including in data verification, visualization, and other medical evaluative and diagnostic settings.

The radiotherapy system includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160. As an example, the radiotherapy processing computing system 110 can be configured to perform treatment plan design, generation, and implementation by executing instructions or data from the treatment processing logic 120, as part of operations to generate and customize radiation therapy treatment plans to be used by the treatment device 180.

The radiotherapy processing computing system 110 may include processing circuitry 112, memory 114, a storage device 116, and other hardware and software-operable features such as a user interface 142, a communication interface (not shown), and the like. The storage device 116 may store computer-executable instructions, such as an operating system, radiation therapy treatment plans (e.g., original treatment plans, training treatment plans, generated treatment plans, adapted or modified treatment plans and the like), software programs (e.g., radiotherapy treatment plan software, image or anatomical visualization software, AI implementations and algorithms such as provided by DL models, ML models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processing circuitry 112 can execute sequences of computer program instructions, stored in memory 114, and accessed from the storage device 116, to perform various operations, processes, methods that will be explained in greater detail below.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a machine-readable medium on which is stored one or more sets of instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting machine-readable media.

The memory device 114 and the storage device 116 may constitute a non-transitory computer-readable medium. For example, the memory device 114 and the storage device 116 may store or load instructions for one or more software applications on the computer-readable medium. Software applications stored or loaded with the memory device 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory device 114 and the storage device 116 may store or load an entire software application, part of a software application, or code or data that is associated with a software application, which is executable by the processing circuitry 112. In a further example, the memory device 114 and the storage device 116 may store, load, and manipulate one or more radiation therapy treatment plans, imaging data, segmentation data, treatment visualizations, histograms or measurements, AI model data (e.g., weights and parameters), labels and mapping data, etc. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the radiotherapy processing computing system 110 may obtain image data 152 from the image data source 150, for hosting on the storage device 116 and the memory 114. In an example, the software programs operating on the radiotherapy processing computing system 110 may convert medical images of one format (e.g., MRI) to another format (e.g., CT), such as by producing synthetic images, such as a pseudo-CT image. In another example, the software programs may register or associate a patient medical image (e.g., a CT image or an MR image) with that patient's dose distribution of radiotherapy treatment (e.g., also represented as an image) so that corresponding image voxels and dose voxels are appropriately associated. In yet another example, the software programs may substitute functions of the patient images such as signed distance functions or processed versions of the images that emphasize some aspect of the image information. Such functions might emphasize edges or differences in voxel textures, or other structural aspects. In another example, the software programs may visualize, hide, emphasize, or de-emphasize some aspect of anatomical features, segmented features, or dose or treatment information, within medical images. The storage device 116 and memory 114 may store and host data to perform these purposes, including the image data 152, patient data, and other data required to create and implement a radiation therapy treatment plan and associated segmentation operations.

In an example, the radiotherapy processing computing system 110 may obtain or communicate planning data 162 from or to a treatment data source 160, such as a data repository used to manage radiotherapy doses and outputs from the treatment device 180. In an example, the treatment data source 160 includes planning data maintained for a plurality of human subjects, including treatment planning parameters (e.g., doses, measurements, treatment parameters) for individual patients at different times. In an example, the treatment data source 160 includes training data and previously designed or approved treatment plans and treatment mappings (e.g., treatment plans identified as "gold standard" or "optimal" based on safety, efficacy, efficiency, or other medical assessments). In further examples, the treatment data source 160 receives or updates the planning data 162 as a result of a treatment plan generated by the treatment plan generation workflow 130; the treatment data source 160 may also provide or host the planning data for use in the treatment plan training workflow 140.

The processing circuitry 112 may be communicatively coupled to the memory 114 and the storage device 116, and the processing circuitry 112 may be configured to execute computer executable instructions stored thereon from either the memory 114 or the storage device 116. The processing circuitry 112 may execute instructions to cause medical images from the image data 152 to be received or obtained in memory 114, and processed using the treatment processing logic 120. For example, the radiotherapy processing computing system 110 may receive image data 152 from the image acquisition device 170 or image data sources 150 via a communication interface and network to be stored or cached in the storage device 116. The processing circuitry 112 may also send or update medical images stored in memory 114 or the storage device 116 via a communication interface to another database or data store (e.g., a medical facility database). In some examples, one or more of the systems may form a distributed computing or virtualized environment that uses a network to collaboratively perform the embodiments described herein. In addition, such network may be connected to internet to communicate with servers and clients that reside remotely on the internet.

In further examples, the processing circuitry 112 may utilize software programs (e.g., a treatment planning software) along with the image data 152 and other patient data to create a radiation therapy treatment plan. In an example, the image data 152 may include or be accompanied by anatomical or diagnostic information such as data associated with a patient anatomical region, organ, or volume of interest segmentation data. Patient data may include information such as (1) functional organ modeling data (e.g., serial versus parallel organs, appropriate dose response models, etc.); (2) radiation dosage data (e.g., dose-volume histogram (DVH) information, comparisons, or the like); or (3) other clinical information about the patient and course of treatment (e.g., other surgeries, chemotherapy, previous radiotherapy, etc.). In a further example, the planning data 162 is specifically associated or linked to segmentation or labeling of anatomical features and associated dose information for such anatomical features, that is specific to the patient, a set of patients, a procedure or type of treatment, a set of procedures or treatments, an image acquisition device, a medical facility, or the like. Consistent with the following examples, the planning data 162 and the treatment data sources 160, and the associated trained models, may be maintained for a single medical condition or radiotherapy treatment, or multiple types of medical conditions or radiotherapy treatment.

In addition, the processing circuitry 112 may utilize software programs to generate intermediate data such as updated parameters to be used, for example, by a neural network model, machine learning model, treatment plan generation workflow 130, treatment plan training workflow 140, or other aspects involved with generation of a treatment plan with a GAN as discussed herein. Further, such software programs may utilize the treatment processing logic 120 to implement the treatment plan generation workflow 130 to produce a new or updated plan for deployment to the treatment data source 160, based on the dose information determined using the techniques further discussed herein. The processing circuitry 112 may subsequently then transmit the new or updated plan via a communication interface and the network to the treatment device 180, where the radiation therapy plan will be used to treat a patient with radiation via the treatment device 180, consistent with results of the workflow 130 as trained with the workflow 140. Other outputs and uses of the software programs and the workflows 130, 140 may occur with use of the radiotherapy processing computing system 110.

In the examples herein (e.g., with reference to the generative adversarial network processing discussed with reference to FIGS. 3 and 4, and the dose and anatomical data processing discussed with reference to FIGS. 5 to 8), the processing circuitry 112 may execute software programs that invokes the treatment processing logic 120 to implement functions of ML, DL, neural networks, and other aspects of automatic processing and artificial intelligence for treatment plan generation. For instance, the processing circuitry 112 may execute software programs that train, analyze, predict, and evaluate a treatment plan (and dose information for the treatment plan) based on a medical image, a medical image derivation, an anatomical area mapping, radiotherapy treatment or treatment device constraints, or other considerations of a treatment plan as discussed herein.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 152 may also include or be associated with medical image processing data, for instance, training images, and ground truth images, contoured images, and dose images. In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., a MRI device combined with a linear accelerator, also referred to as an "MRI-Linac"). Such an MRI-Linac can be used, for example, to determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like. In some examples, the use of the GAN-trained models in the treatment plan generation workflow 130 is used to only generate a dose representation (e.g., dose amounts) in a particular anatomical area, and other workflows or logic (not shown) are used to translate this dose representation into the specific beam angles and radiation physics used to accomplish the radiotherapy treatment.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may in some examples have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device which outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.) treatment plans, a target, localizing a target and/or tracking a target, or any related information to the user. The input device 148 connected to the user interface 142 may be a keyboard, a keypad, a touch screen or any type of device that a user may input information to the radiotherapy system. Alternatively, the output device 146, the input device 148, and features of the user interface 142 may be integrated into a single device such as a smartphone or tablet computer, e.g., Apple iPad®, Lenovo Thinkpad®, Samsung Galaxy®, etc.

Furthermore, any and all components of the radiotherapy system may be implemented as a virtual machine (e.g., via VMWare, Hyper-V, and the like virtualization platforms). For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The treatment processing logic 120 or other software programs may cause the computing system to communicate with the image data sources 150 to read images into memory 114 and the storage device 116, or store images or associated data from the memory 114 or the storage device 116 to and from the image data sources 150. For example, the image data source 150 may be configured to store and provide a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) metadata, etc.) that the image data source 150 hosts, from image sets in image data 152 obtained from one or more patients via the image acquisition device 170 in model training or generation use cases. The image data source 150 or other databases may also store data to be used by the treatment processing logic 120 when executing a software program that performs treatment plan operations of creating, modifying, or estimating radiation therapy treatment plans. Further, various databases may store the data produced by the trained models, including the network parameters constituting the models learned by the generative adversarial network model 138 and the resulting predicted data. The radiotherapy processing computing system 110 thus may obtain and/or receive the image data 152 (e.g., 2D MRI slice images, CT images, 2D Fluoroscopy images, X-ray images, 3DMRI images, 4D MRI images, etc.) from the image data source 150, the image acquisition device 170, the treatment device 180 (e.g., a MRI-Linac), or other information systems, in connection with performing radiation treatment or diagnostic operations.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 170 in "near real-time" while a patient is undergoing radiation therapy treatment, for example, when using the treatment device 180 (with "near real-time" meaning acquiring the data in at least milliseconds or less).

The treatment processing logic 120 in the radiotherapy processing computing system 110 is depicted as implementing a treatment plan generation workflow 130 which involves the use of a trained (learned) generative model (e.g., implementing the method described below with reference to FIG. 10). This generative model may be provided by a generator 138B trained as part of a generative adversarial network model 138. In an example, the plan generation workflow 130 operated by the treatment processing logic 120 integrates with use of anatomy data processing 132 (e.g., to process input image data reflecting an anatomical area of treatment, in connection with the generative model discussed herein), dose data processing 134 (e.g., to produce output image data reflecting a radiotherapy dose mapped to the anatomical area of treatment, in connection with the generative model discussed herein), and plan data processing 136 (e.g., to establish a treatment plan based on the mapped radiotherapy dose and other constraints, as discussed herein). Other plan generation, evaluation, and verification functionality not expressly depicted may be incorporated into the treatment plan generation workflow 130.

In an example, the generator 138B includes learned weights and values as a result of a training involving use of a discriminator 138A and the generator 138B in the GAN 138, in connection with a treatment plan training workflow 140 that processes pairings of training data (e.g., parings of model or predefined anatomy data and dose data). As indicated above, this training workflow 140 may obtain and utilize training data from the data sources 160, 170, and associated planning data 162 and image data 152.

The treatment processing logic 120 and the treatment plan generation workflow 130 may be used when generating the radiation therapy treatment plan, within use of software programs having radiotherapy treatment planning features, such as Monaco®, manufactured by Elekta AB of Stockholm, Sweden. In order to generate the radiation therapy treatment plans, the radiotherapy processing computing system 110 may communicate with the image acquisition device 170 (e.g., a CT device, a MRI device, a PET device, an X-ray device, an ultrasound device, etc.) to capture and access images of the patient and to delineate a target, such as a tumor. In some examples, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 170 to reveal the internal structure of a body part. Based on the information from the medical images, a 3D structure and segmentation, labeling, or other identification of the relevant anatomical portion(s) may be obtained, using any combination of automated or human-assisted functions. For example, segmentation and labeling may be deployed in connection with the identification of treatment areas and restricted areas (e.g., areas to avoid treatment), such as with the identification and definition of planning treatment volumes (e.g., to deliver radiotherapy to a tumor or organ of interest) and OAR(s) (e.g., to avoid radiotherapy and radiation exposure in certain organs or tissue areas). Two-dimensional illustrations of these types of segments and anatomical areas to avoid or target for treatment are further depicted in FIG. 7.

Accordingly, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS®, manufactured by Elekta AB of Stockholm, Sweden). Thus, in certain examples, the 2D or 3D structure of a target tumor or an OAR may be generated automatically by the treatment planning software.

In prior approaches, after the target tumor and the OAR(s) have been located and delineated, a dosimetrist, physician, or healthcare worker would determine a specific dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning would be performed to determine one or more treatment plan parameters that would achieve the desired radiation dose distribution. The effectiveness of such approaches are thus limited to the human expertise and capability applied for such planning activity. The use of the treatment processing logic 120 and the treatment plan generation workflow 130 discussed herein is designed to provide an automated mechanism by which AI and ML techniques can produce an improved estimate or prediction of such dose distribution information.

In addition to dose amounts, additional examples of treatment plan parameters (e.g., that may be generated by plan data processing 136, or other functions of the plan generation workflow 130) include volume delineation parameters (e.g., which define target volumes, contour sensitive structures, etc.), margins around the target tumor and OARs, beam angle selection, collimator settings, and beam-on times. Accordingly, during planning processes, the physician or other healthcare worker may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). Each of these functions or constraints may be replaced, enhanced, or enforced through the use of the treatment plan generation workflow 130 discussed herein.

The result of the treatment processing logic 120 and the treatment plan generation workflow 130 may produce a radiation therapy treatment plan that may be stored and provided (e.g., as planning data 162 or to data source 160). Some of these treatment parameters may be correlated or coordinated with specific treatment objectives and attempts. For example, tuning one parameter (e.g., weights for different objectives, such as increasing the dose to the target tumor) in an attempt to change the treatment plan may affect at least one other parameter, which in turn may result in the development of a different treatment plan. Thus, the radiotherapy processing computing system 110 may generate a tailored radiation therapy treatment plan that considers these and like parameters in order for the treatment device 180 to provide suitable radiotherapy treatment to the patient.

Figure 2:
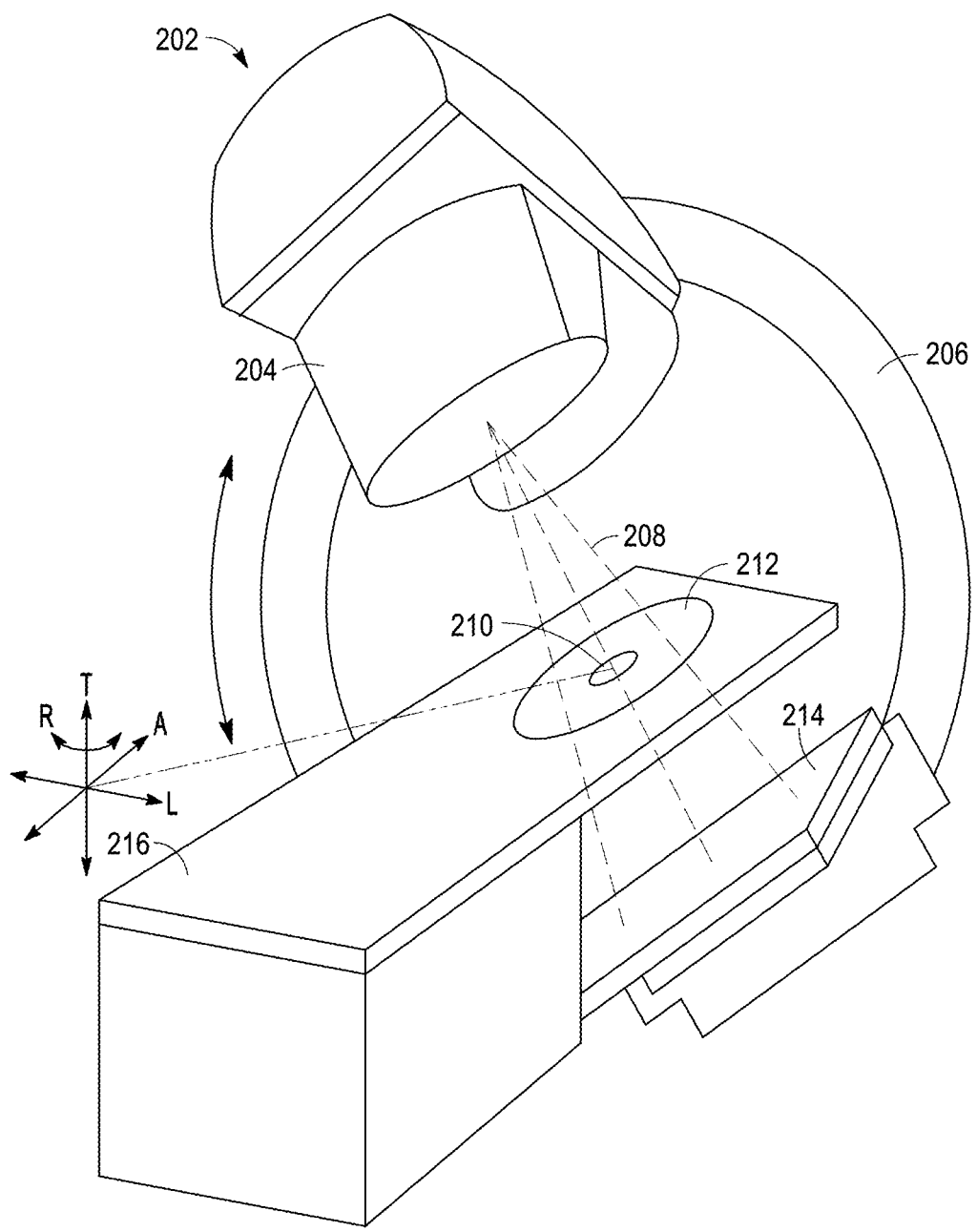
FIG. 2 illustrates an exemplary image-guided radiotherapy device.

FIG. 2 illustrates an exemplary image-guided radiotherapy device 202, that includes include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC). As will be understood, the radiation therapy output 204 may be provided in connection with the treatment processing logic 120 which implements a treatment plan generation workflow 130 and the associated use of a treatment plan from a generative model 138B of a GAN.

As an example, a patient can be positioned in a region 212, supported by the treatment couch 216 to receive a radiation therapy dose according to a radiation therapy treatment plan (e.g., a treatment plan generated by the radiotherapy system of FIG. 1). The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an example, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiation therapy device 202 may be integrated within the radiotherapy system or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

As specific examples of radiotherapy, Intensity modulated radiotherapy (IMRT) and volumetric modulated arc therapy (VMAT) are commonly used in current radiotherapy practice, and are designed to produce more exact dose to targets with corresponding sparing of neighboring sensitive tissues than earlier treatment methods. IMRT planning proceeds through two stages: 1) the creation of a fluence map depicting the localized deposition of energy in the patient, and 2) the translation of the fluences for each beam into a sequence of MLC apertures that shape the beam boundary and modulate its intensity profile. This is the basic procedure for step-and-shoot IMRT. It is in the first stage that the planning must resolve the conflicting constraints for prescribed target dose and organ sparing. The fluence map optimization (FMO) problem encapsulates the treatment planning features and constraint conflicts.

In IMRT, a patient has a set of defined targets and sensitive organs. The dose received by a voxel is a linear function of beamlet intensities or weights:

$$D_{js}(b) = \sum_{i=1}^{n} D_{ijs} b_i, \quad j = 1, \ldots, v_s, \quad s = 1, \ldots, S \quad \text{(EQUATION 1)}$$

where $D_{js}(b)$ is the dose deposited in voxel j in structure s from beamlet i at unit intensity, the intensity or weight of beamlet i is denoted by $x_i$, and the vector of n beamlet weights is $b=(b_1, \ldots, b_n)^T$ where superscript T indicates the vector transpose. S is the total number of structures, where the first T of them are targets (T<S), and $v_s$ is the number of voxels in structure $s \in S$. The dose distribution in structures is $$D_s(b) = (D_{1s}(b), \ldots, D_{v_s s}(b)), s = 1, \ldots, S \quad \text{(EQUATION 2)}$$

that could represent one point in a $v_s$-dimensional dose space.

Multi-criteria optimization has been usefully applied to the FMO problem. For example, a known approach provides the following FMO model formulation, $$(P): \min_{x \geq 0} F(D(b)) \quad \text{(EQUATION 3)}$$
$$\text{s.t. } \min_{x \geq 0} G_1(b) \leq C_1(b)$$
$$\min_{x \geq 0} G_2(b) \leq C_2(b)$$
$$\ldots$$
$$\min_{x \geq 0} G_L(b) \leq C_L(b)$$

where F(D(b)) is a dose objective function whose minimization is subject to the listed constraints, where specialized objectives G(b) are subject to dose constraints C(b), and L is the number of constraints. The objective F(D(b)) will minimize the difference of the dose being calculated d(b) with the prescribed dose $$F(D(b)) = \Sigma_i \Sigma_j \Sigma_s \max\{0 \| d_{ijs}(b) - P_{ijs}(b) \|_2^2\} \quad \text{(EQUATION 4)}$$

Another solution to the FMO problem can be obtained using the method of Lagrange multipliers. Given the objective and constraints above, the Lagrange function is defined as, $$\Lambda(b,\lambda) = F(D(b)) + \Sigma_{l \in L} \lambda_l (G_l(b) - C_l(b)), \lambda = (\lambda_1, \ldots, \lambda_L)^T \quad \text{(EQUATION 5)}$$

or, for normalized constraint functions $g_l(x)$, $$\Lambda(b,\lambda) = F(D(b)) + \Sigma_{l \in L} \lambda_l g_l(b), g_l(b) = G_l(b)/C_l(b) - 1, \lambda_l = (\lambda_1, \ldots, \lambda_L)^T \quad \text{(EQUATION 6)}$$

and the stationary point (zero-valued partial derivatives $\partial F/\partial x_i$ and $\partial g_l/\partial x_i$) solution is obtained for, $$\nabla_b \Lambda(b,\lambda) = \nabla_b F(D(b)) + \Sigma_{l \in L} \lambda_l \nabla_b g_l(b) = 0 \quad \text{(EQUATION 7)}$$

where the values of the individual $\lambda_l$ are varied to obtain the solution, subject to the conditions $\lambda_l > 0$, $\Sigma_{l \in L} \lambda_l = 1$. The prior equation (Equation 7) is solved iteratively by conjugate gradient descent to obtain a set of beamlet weights $b^* = \arg\min_b \nabla_b \Lambda(b,\lambda)$ that satisfy the equation to the maximum extent possible.

The individual constraints are either target constraints of the sort, "95% of target 1 shall receive no less than 95% of the prescription dose" or "98% of target 1 shall receive the prescribed dose," or "the maximum allowed dose within target 1 is 107% of the prescribed dose to a volume of at least 0.03 cc." Thus, critical structures for which dose is to be limited are described by constraints of the sort "no more than 15% volume of structure 1 shall exceed 80 Gy" or "mean dose to structure 1 will be less than or equal to 52 Gy."

In sum, the target objectives are maximized, the critical structure constraints are minimized (structure doses are less than the constraint doses), and the beamlet weights are all greater than or equal to zero. In practice, the target and critical structure constraints are usually in conflict since the target dose penumbra due to scatter frequently overlaps with nearby critical structures. Planning that involves the iterative adjustment of the constraint weights to produce desired 3D dose distributions can produce non-intuitive results and require significant planner time and effort since each weight adjustment must be followed by a re-solution of the gradient Lagrangian).

The FMO problem to be solved for VMAT is similar to IMRT, except the beamlets are arranged in many more beams around the patient. The VMAT treatment is delivered by continuously moving the gantry around the patient, and with continuously-moving MLC leaves that reshape the aperture and vary the intensity pattern of the aperture. VMAT treatments can be delivered faster and with fewer monitor units (total beam on-time) than IMRT treatments for the same tumor. Because of the larger number of effective beams, VMAT is potentially more accurate in target coverage and organ sparing than the equivalent IMRT treatment.

Finally, the fluence map obtained as described here is only the intermediate result in IMRT/VMAT planning. From the 3D fluence map, a 3D dose distribution is computed that has to satisfy the gantry- and MLC leaf-motion constraints to produce a dose map that differs as little as possible from the fluence map. This is the segmentation part of the planning process, and is also a constrained optimization problem.

These operations of radiotherapy planning can be improved with uses of deep learning (DL)/machine learning (ML) approaches involving a GAN as discussed herein. AI, DL, or ML are all based on mathematical analyses of random variable probabilities and their probability distributions. Typically random variables are observed as pairs X, Y, $\{x_i, y_i\}$, i=1, N, where for each value $x_i \in X$ we wish to assign it to a class or category represented by the scalar category index $y_i \in Y$ (classification), or assign it a numeric value according to some function $y_i = f(x_i)$ (regression).

All classification or regression methods rely on the concept of probability distributions to describe the random variables X, Y. The probability distribution for random variable X, p(x) (x is either discrete or continuous) must satisfy: 1) the domain of p(x) must be the set of all possible values of x, 2) for all $x \in X$, $p(x) \geq 0$, and $$3) \int_X p(x)dx = 1.$$

A sample x drawn from distribution p(x) is written x~p(x). The joint distribution of X, Y is written p(x, y) and the marginal distribution of x, p(x) given the joint distribution p(x, y) is $p(x) = \int p(x, y) dy$. The probability of observing y conditioned on the value of x is $p(y|x) = p(x, y)/p(x)$. The conditional probability of observing y given data x is called the data likelihood. Bayes' rule connects the X, Y conditional likelihoods as $p(y|x) = p(x|y)p(y)/p(x)$.

The goal of statistical learning is to determine a mapping $f: x \to y$ that associates any y with an x. One of the most important methods is maximum likelihood estimation. The training data are assumed to be generated by a process $p_{data}(x, y)$. Finding the mapping involves learning a model process $p_{model}(x; \theta)$ that includes parameters $\theta$ that the mapping is dependent on in addition to x. For example, the $\theta$ may include neural network layer weights and bias parameters. Maximum likelihood estimates the parameters $\theta_L$ that give the most likely values of x as $$\theta_L = \arg\max_\theta E_{x \sim p_{data}}[\log p_{model}(x; \theta)] \quad \text{(EQUATION 8)}$$

where E is the expected value of the bracketed argument. Since probability distributions are difficult to approximate, and since the goal is to minimize the difference between the $p_{data}(x)$ and the $p_{model}(x; \theta)$ distributions, the KL divergence provides a data-driven alternative, $$D_{KL}(p_{data} \| p_{model}) = E_{x \sim p_{model}}[\log p_{data}(x) - \log p_{model}(x)] \quad \text{(EQUATION 9)}$$

where the maximum likelihood is equivalent to minimizing the difference between the model and data distributions. The log $p_{data}(x)$ term is independent of the model so that to minimize $D_{KL}$ one needs to minimize, $$-E_{x \sim p_{data}}[\log p_{model}(x)] \quad \text{(EQUATION 10)}$$

which is the same as Equation (8) with the $\theta$ implied in model expression. The desired mapping is then $f(\theta): x \sim p_{model} \to y$.

The presently disclosed system for radiotherapy dose distribution modeling and treatment plan estimation provides a useful application of modern neural network technology to model radiotherapy treatment planning. Neural networks (NNs) have been studied since the 1960's for solutions to classification problems (assigning observed data x to one of two or more classes $y_i$, i=1, ..., n) and regression problems (associating observed data x with the value y of a parameter pertaining to that data). The generation of treatment parameters and dose distributions may be considered a regression problem, which is produced through the use of a NN generative model learned through a GAN configuration.

Simple NNs consist of an input layer, a middle or hidden layer, and an output layer each containing computational units or nodes. The hidden layer(s) nodes have input from all the input layer nodes and are connected to all nodes in the output layer. Such a network is termed "fully connected." Each node communicates a signal to the output node depending on a nonlinear function of the sum of its inputs. For a classifier the number of input layer nodes typically equals the number of features for each of a set of objects being sorted into classes, and the number of output layer nodes is equal to the number of classes. A network is trained by presenting it with the features of objects of known classes, and adjusting the node weights to reduce the training error by an algorithm called backpropagation. Thus trained, the network can classify novel objects whose class is unknown.

Neural networks have the capacity to discover relationships between the data and classes or regression values, and under certain conditions, can emulate any function y=f(x) including non-linear functions. This is particularly relevant to the problem of dose prediction and plan modelling, because the shape or volume overlap relationships of targets and organs as captured in the dose-volume histogram and the overlap-volume histogram are highly non-linear and have been shown to be associated with dose distribution shape and plan quality.

In ML, an assumption is that the training and test data are both generated by the same data-generating process, $p_{data}$ in which each $\{x_i, y_i\}$ sample is identically and independently distributed (i.i.d.). In ML, the goals are to minimize the training error and to make the difference between the training and test errors as small as possible. Underfitting occurs if the training error is too large; overfitting occurs when the train-test error gap is too large. Both types of performance deficiency are related to model capacity; large capacity may fit the training data very well but lead to overfitting; small capacity may lead to underfitting. Since DNNs have enormous capacity, overfitting is a more common concern in machine learning.

Deep learning is a machine learning method employing DNNs with large numbers of hidden layers with inputs and outputs arranged in complex ways, and producing human level performance on image and speech recognition tasks. In the present examples, the DNNs will be trained to determine the relationship between observed data X and an output Y. The data $X = \{x_1, \ldots, x_n\}$ is a collection of 3D planning CT images, anatomy voxel label maps, and planning metadata (beam gantry angles, beamlet vectors, etc.) and the output Y is a 3D map of dose or fluence in the planning image coordinate system.

In some examples, a mapping of fluence may be preferred to dose because fluence represents the product of the planning process to be modelled. Dose is the result of FMO plus the generation of aperture segments, an algorithm independent of the FMO process. Dose maps are routinely produced by treatment planning programs, whereas fluence maps are not always available.

The action of the DNN is symbolically captured by the function $f(\bullet)$ $$Y^* = f(X; \Theta) \quad \text{(EQUATION 11)}$$

where $\Theta = (\theta_1, \ldots, \theta_n)^T$ is a vector of the parameters pertaining to the trained NN for which the Y* is the closest approximation of the true Y observed in training. The DNN is trained using data sets $\{X, Y\}_i$, i=1, ..., N of images and labels X and known dose/fluence maps Y. Training minimizes a cost function J(Θ) of the sort $$J(\Theta^*) = \arg\min_\Theta \|Y - Y^*\|^2 \quad \text{(EQUATION 12)}$$

where Θ* is the set of parameters that minimizes the mean squared error between the actual Y and the estimate Y*. In deep learning, the cost functions frequently express the data approximation function as a probabilistic function of the problem variables, or the conditional likelihood of observing Y given X and subject to the values of the parameters Θ, expressed as P(Y|X; Θ), for which the optimal parameters $\Theta_{HL}$ are obtained by maximizing the likelihood, $$\Theta_{ML} = \arg\max_\Theta P(Y|X; \Theta) \quad \text{(EQUATION 13)}$$

or alternatively $$\Theta_{ML} = \arg\max_\Theta \sum_{i=1}^{T} \log P(Y_i | X_i; \Theta). \quad \text{(EQUATION 14)}$$

summed over the training data.

The DNN output that results in the identification of voxels belonging to anatomy classes is an example of classification. In this case, the DNN output will be the real valued elements $y_i$ of the dose map $Y = (y_1, \ldots, y_M)^T$ meaning that the network computation will be an example of regression. The dose map Y can then be used for several purposes: 1) to compare with existing patient plan dose maps and corresponding DVHs for QA, 2) to provide starting points for subsequent planning or re-planning, and 3) with sufficient training and development, to provide automated planning. A map of fluence could serve an equivalent purpose, except that a translation into a deliverable plan with dose distribution would have to be computed using a treatment planning program. As noted above, the fluence map could provide a clearer model of the planning process.

DNNs have many more layers (are much deeper) than basic NN implementations, as DNNs often include dozens or hundreds of layers, each layer composed of thousands to hundreds of thousands of nodes, with the layers arranged in complex geometries. In addition to weighted sums of inputs, some layers compute other operations on the prior layer outputs such as convolution. Convolutions and the filters derived from them can locate edges in images, or temporal/pitch features in sound streams, and succeeding layers find larger structures composed of these primitives. Such trained DNNs which involve the use of convolutional layers are referred to as convolutional neural networks (CNNs).

An important CNN architectural innovation is the skip connections. Originally introduced to improve accuracy and shorten training, skip connections splice nodal data at one level of a network with that of nodes at another level. An important example is the U-Net architecture developed for medical image segmentation. As further discussed below, the "left" part of the "U" encodes the image data as convolution filter features and the "right" part of the "U" decodes those features onto successive higher-resolution representations. The combination of encoded and decoded features across the same network hierarchy levels leads to more accurate classifications. Another variation of a skip connection is implemented within each CNN block forcing training on differences (residuals) between layer outputs instead of the layer outputs directly. This "ResNet" architecture and its many variants can produce improved NN accuracy.

Figure 3:
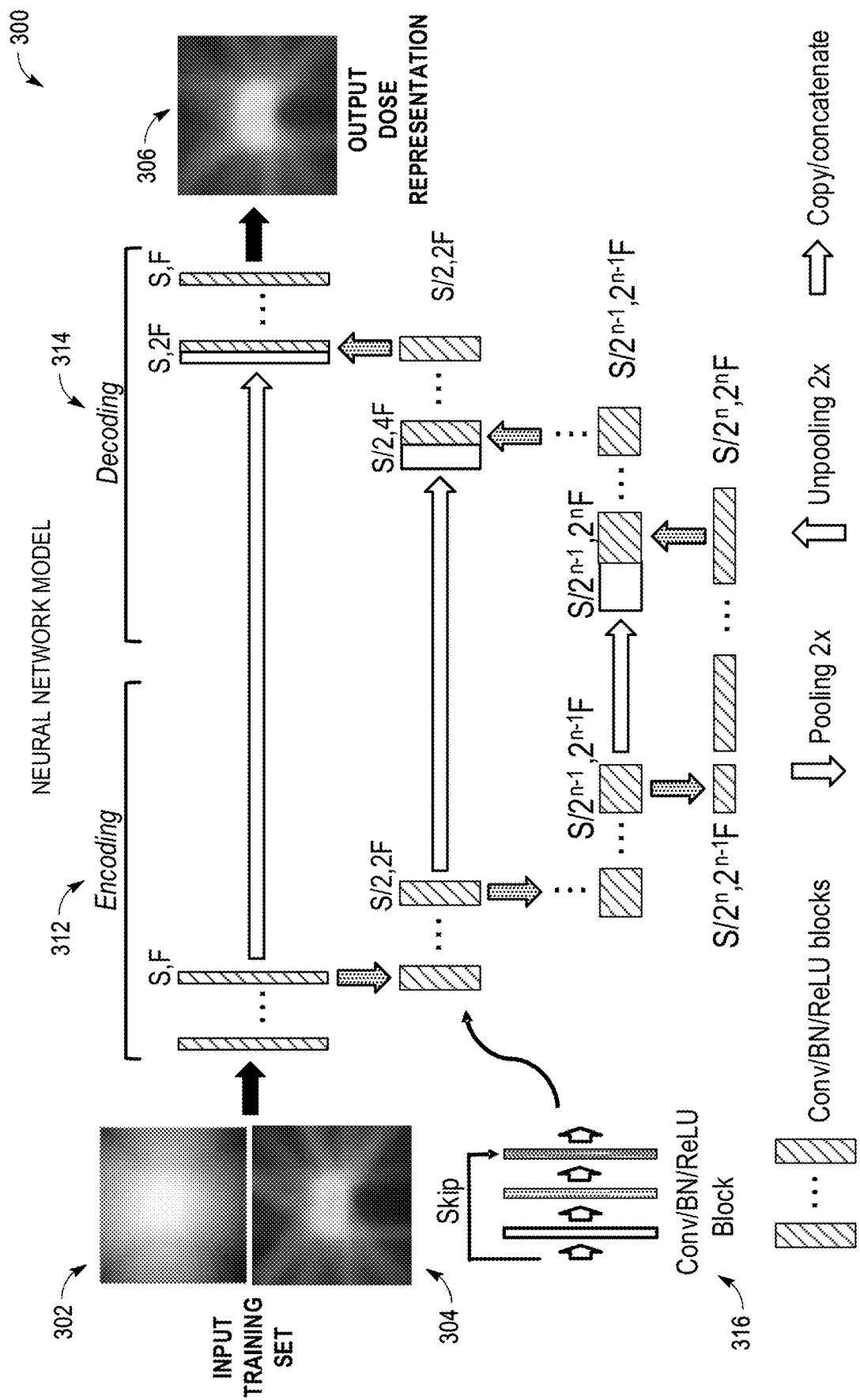
FIG. 3 illustrates an exemplary convolutional neural network model adapted for generating a treatment dose model.

FIG. 3 illustrates an exemplary CNN model 300 adapted for generating a treatment dose model according to the present disclosure. Specifically, the model 300 depicts an arrangement of a "U-Net" deep CNN designed for generating an output data set (an output dose representation 306, e.g., a dose image) based on an input training set (e.g., anatomical area representation 302, e.g., a mapping image, and a dose map 304, e.g., a dose mapping image). The name derives from the "U" configuration, and as is well understood, this form of a NN model can produce pixel-wise classification or regression results.

The left side of the model operations (the "encoding" operations 312) learns a set of features that the right side (the "decoding" operations 314) uses to reconstruct an output result. The U-Net has n levels consisting of conv/BN/ReLU (convolution/batch normalization/rectified linear units) blocks 316, and each block has a skip connection to implement residual learning. The block sizes are denoted in FIG. 3 by "S" and "F" numbers; input images are S×S in size, and the number of feature layers is equal to F. The output of each block is a pattern of feature responses in arrays the same size as the images.

Proceeding down the encoding path, the size of the blocks decreases by ½ or $2^{-1}$ at each level while the size of the features by convention increases by a factor of 2. The decoding side of the network goes back up in scale from $S/2^n$ while adding in feature content from the left side at the same level—this is the copy/concatenate data communication. The input images 302, 304 shown in FIG. 3 are provided for training the network to evaluate the conv/BN/ReLU layer parameters, as there would be no output image. For inference, or testing, with use of the model, the input would be a single image of the anatomy representation (binary masks or signed distance map sections) and the output would be a dose estimate image 306.

The representation of the model 300 of FIG. 3 thus illustrates the training and prediction of a generative model, which is adapted to perform regression rather than classification. Consistent with embodiments of the present disclosure, the treatment modeling methods, systems, devices, and/or processes based on the such models include two stages: training of the generative model, with use of a discriminator/generator pair in a GAN; and prediction with the generative model, with use of a GAN-trained generator. Various examples involving a GAN and a conditional GAN (cGAN) for treatment plan images are discussed in detail in the following examples. It will be understood that other variations and combinations of the type of deep learning model and other neural-network processing approaches may also be implemented with the present techniques. Further, although the following examples are discussed with reference to images and image data, it will be understood that the following networks and GAN may operate with use of other non-image data representations and formats.

In Deep CNN training, the learned model is the values of layer node parameters θ (node weights and layer biases) determined during training. Training employs maximum likelihood or the cross entropy between the training data and the model distribution. A cost function expressing this relationship is $$J(\theta) = -E_{x,y \sim p_{data}} \log p_{model}(y|x) \quad \text{(EQUATION 15)}$$

The exact form of the cost function for a specific problem depends on the nature of the model used. A Gaussian model $p_{model}(y|x)=N(y: f(x; \theta))$ implies a cost function such as:

$$J(\theta) = \tfrac{1}{2} E_{x, y \sim p_{data}} \|y - f(x;\theta)\|_2^2 + \text{const} \quad \text{(EQUATION 16)}$$

Which includes a constant term that does not depend on $\theta$. Thus, minimizing $J(\theta)$ generates the mapping $f(x;\theta)$ that approximates the training data distribution.

Figure 4:
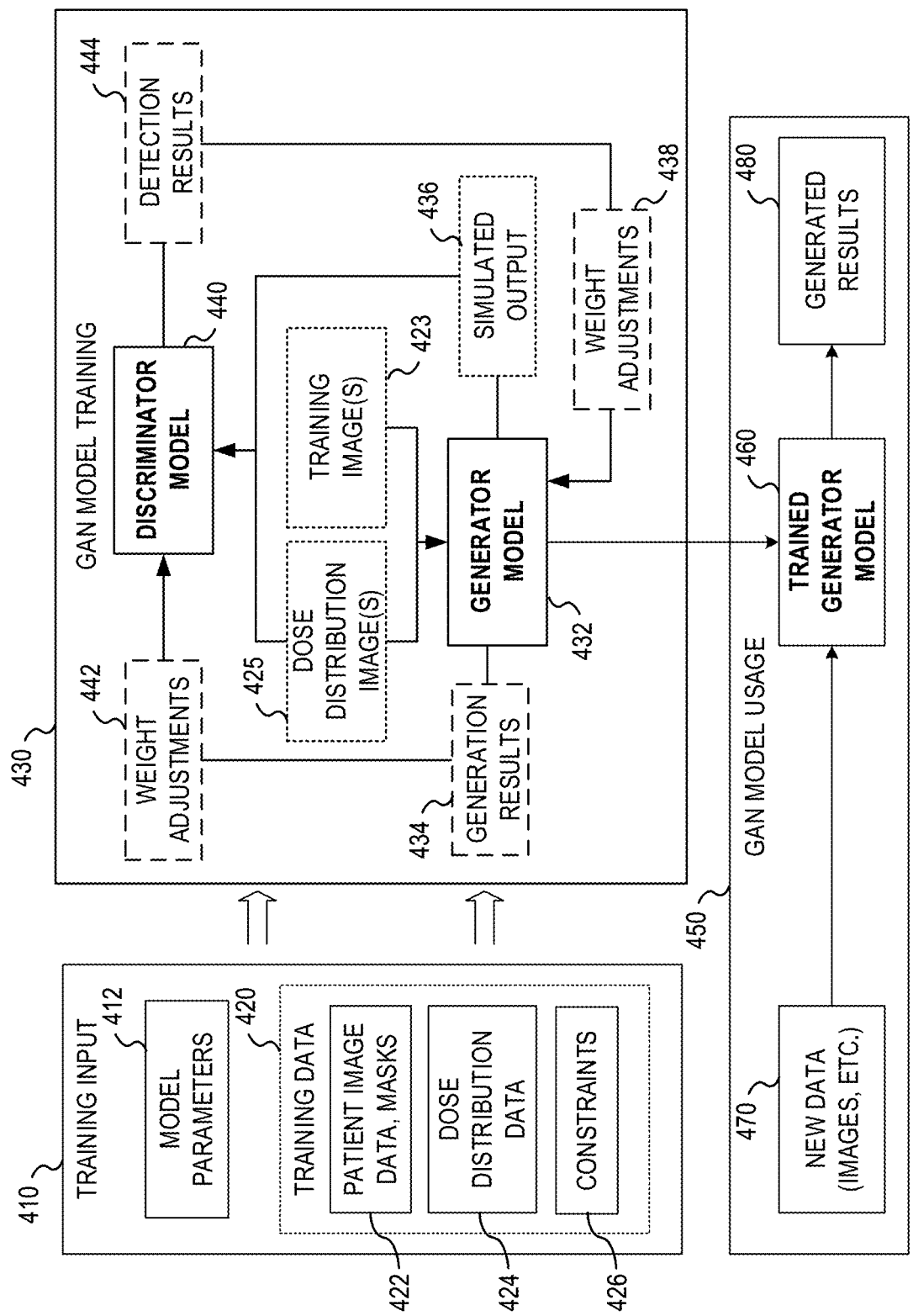
FIG. 4 illustrates an exemplary data flow for training and use of a generative adversarial network adapted for generating a treatment dose model.

FIG. 4 illustrates an exemplary data flow for training and use of a generative adversarial network adapted for generating a treatment dose model. For instance, the generator model 432 of FIG. 4, which is trained to produce a trained generator model 460, may be trained to implement the processing functionality 132, 134, 136 provided as part of the radiotherapy treatment processing logic 120 in the radiotherapy system of FIG. 1. Accordingly, a data flow of the GAN model usage 450 (prediction) is depicted in FIG. 4 as the provision of new data 470 (e.g., input images from a new patient) to a trained generator model 460, and the use of the trained generator model 460 to produce a prediction or estimate of generated results 480.

GANs comprise two networks: a generative network (e.g., generator model 432) that is trained to perform classification or regression and a discriminative network (e.g., discriminator model 440) that samples the generative network's output distribution (e.g., simulated output 436) and decides whether that sample is the same or different from the true test distribution. The goal for this system of networks is to drive the generator network to learn the ground truth model as accurately as possible such that the discriminator net is able to guess the correct origin for generator samples 50% of the time. The discriminator can access the ground truth but the generator only accesses the training data through the response of the detector to the generator's output.

The data flow of FIG. 4 illustrates the receipt of training input 410, including various values of model parameters 412 and training data 420 (with such training data including patient imaging data and image masks or mappings of anatomical areas 422, dose distribution data and mappings of anatomical areas 424, constraints or conditions 426). The training input is provided to the GAN model training 430 to produce a trained generator model 460 used in the GAN model usage 450.

As part of the GAN model training 430, the generator model 432 is trained on anatomical image data and dose image data pairs 423, 425 (also depicted in FIG. 3 as 302, 304), to produce and map segment pairs in the CNN. In this fashion, the generator model 432 is trained to produce a simulated output dose image representation 436 (also depicted in FIG. 3 as 306) based on an input map. The discriminator model 440 decides whether a simulated representation 436 is from the training data or is from the generator (e.g., as communicated between the generator model 432 and the discriminator model 440 with the generation results 434 and the detection results 444). This training process results in backpropagation of weight adjustments 438, 442 to improve the generator model 432 and the discriminator model 440.

Thus, in this example, data preparation for the GAN model training 430 requires an anatomy representation and a dose representation. In an example, the original data includes pairs of CT image sets and corresponding 3D dose distributions, and such CT and dose data may be registered and resampled to a common coordinate frame to produce pairs of anatomy-derived 2D images and dose sections. Specific anatomy representations of such pairs (and derivations of such pairs) are further illustrated and discussed below with reference to FIGS. 7 and 8.

In detail, in a GAN model, the generator (e.g., generator model 432) learns a distribution over the data x, $p_G(x)$, starting with noise input with distribution $p_z(z)$ as the generator learns a mapping $G(z;\theta_G):p_z(z) \rightarrow p_G(x)$ where G is a differentiable function representing a neural network with layer weight and bias parameters $\theta_G$. The discriminator, $D(x;\theta_D)$ (e.g., discriminator model 440) maps the generator output to a binary scalar {true, false}, deciding true if the generator output is from actual data distribution $p_{data}(x)$ and false if from the generator distribution $p_G(x)$. That is, D(x) is the probability that x came from $p_{data}(x)$ rather than from $p_G(x)$.

Figure 5:
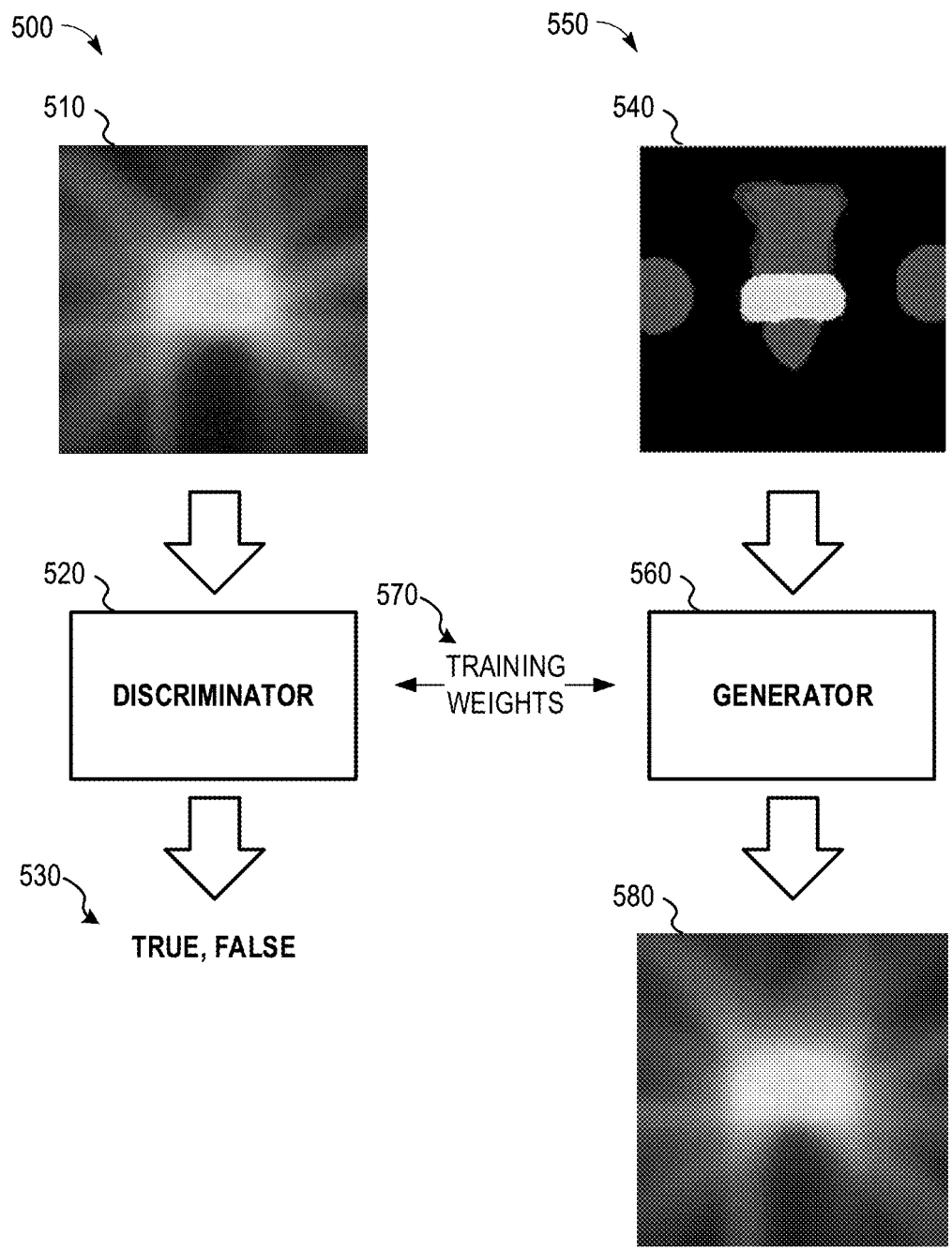
FIG. 5 illustrates training of a generative adversarial network for generating a treatment dose model.
Figure 6:
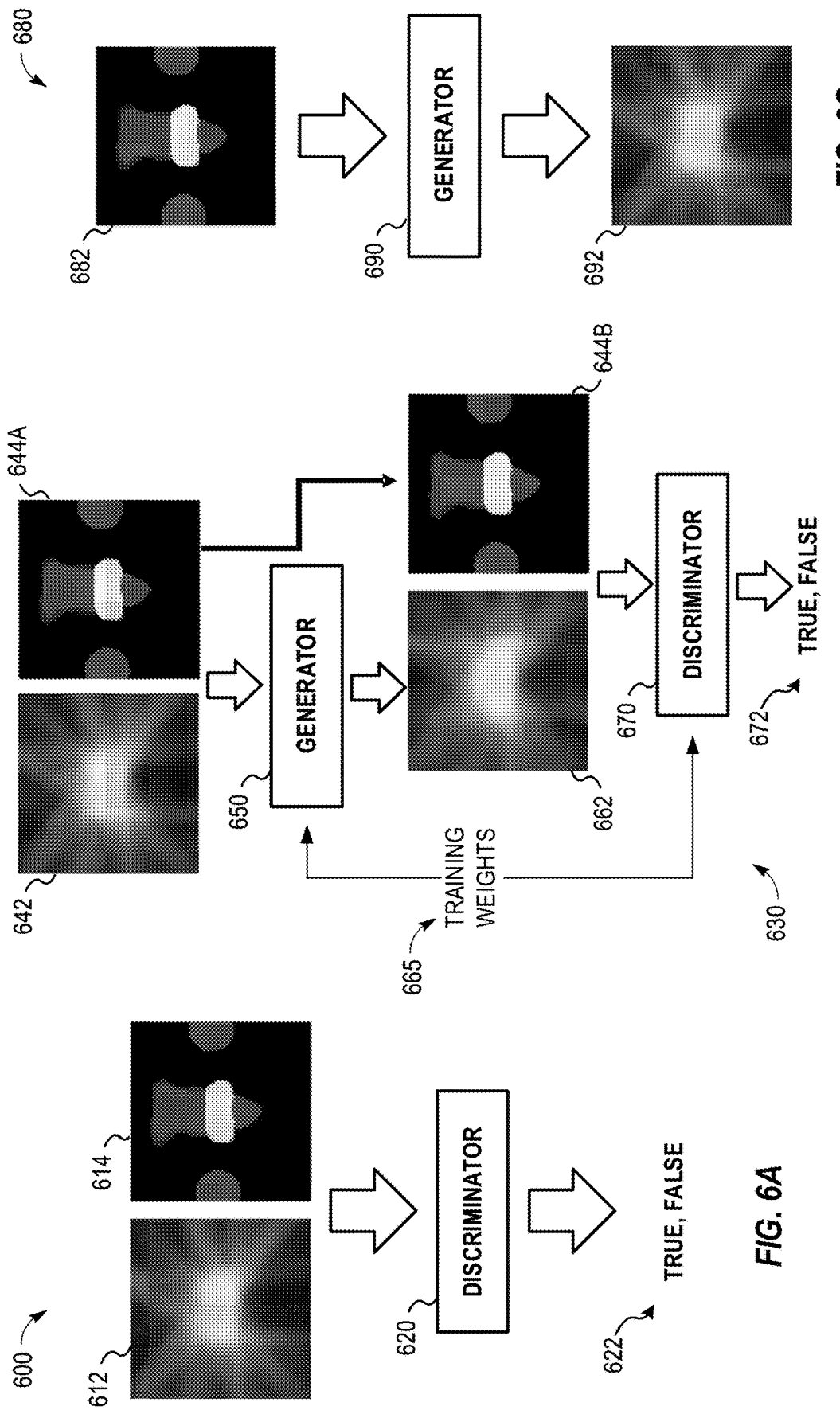
FIGS. 6A, 6B, and 6C illustrate training and use of a conditional generative adversarial network for generating a treatment dose model.

FIG. 5 illustrates training in a GAN for generating a treatment dose model, according to the example techniques discussed herein. FIG. 5 specifically shows the operation flow 500 of a GAN discriminator model D 520, designed to produce a determination value 530 (e.g., true, false) based on an input dose image 510. FIG. 5 also shows the operation flow 500 of a GAN generator model G 560, designed to produce a simulated (e.g., estimated, artificial, etc.) output dose image 580 as a result of an input anatomical mapping image 540.

In the context of the GAN, the discriminator D 520 is trained to maximize the probability of assigning the correct label to samples from both distributions, whereas the generator G 560 is trained to minimize the log(1−D(G(z))), based on adjusted training weights 570 applied during training. D, G can be regarded as playing a two-player minimax game with value function V(D,G) as follows:

$$\min_G \max_D V(D, G) = \quad \text{(EQUATION 17)}$$
$$E_{x \sim p_{data}(x)}[\log D(x)] + E_{z \sim p_z(z)}[\log(1 - D(G(z)))]$$

Early in learning, when G is performing poorly, the log(1−D(G(z))) term dominates V(D,G) and causes early and incorrect termination. Instead of training G to minimize log(1−D(G(z))), G can be trained to maximize log D (G(z)) producing more informative gradients earlier in training. Further, research has also proved that as training progresses, the distribution $p_G(x)$ converges to the true data distribution $p_{data}(X)$.

A useful extension of a GAN is the conditional GAN (cGAN). cGANs extend the GAN model to conditional distributions dependent on additional information available in the problem, including the random variable y observed with x. In the generator G the prior input noise $p_z(z)$ and y can comprise a joint hidden representation, and the adversarial framework can flexibly accommodate this extra information. The two-player minimax game value function can be rewritten as $$\min_G \max_D V(D, G) = \quad \text{(EQUATION 18)}$$
$$E_{x \sim p_{data}(x)}[\log D(x | y)] + E_{z \sim p_z(z)}[\log(1 - D(G(z | y)))]$$

The value of conditioning on y is that the conditional distributions are likely to be more compact and probably more peaked about the mode than the corresponding unconditioned distributions. For a conditional GAN classifier, the models D(x|y) G(z|y) will be restricted to distributions $p_{x\sim data\ x|y}(x|y), G_{z\sim p(z|y)}(z|y)$ instead of the less restricted distributions $p_{x\sim data}(x), G_{z\sim p(z)}(z)$. The conditional distributions would be expected to represent more accurately the specific variance in x,z for a corresponding y.

FIGS. 6A, 6B, and 6C illustrate training and use of a conditional generative adversarial network for generating a treatment dose model. In a similar manner as the operation flow 500 discussed above, FIG. 6A illustrates the operation flow 600 of a discriminator D 620 which produces a determination value 622 (e.g., true, false). However, this determination value 622 is based on two inputs, an input dose image 612 (similar to the dose image 510) and an anatomical mapping image 614 (the condition). Also in a similar manner as the operation flow 550 discussed above, FIG. 6C illustrates the operation flow 680 of a generator G 690 designed to produce a simulated (e.g., estimated, artificial, etc.) output dose image 692 as a result of an input anatomical mapping image 682.

The operation flow 630 of FIG. 6B illustrates how training weights 665 are communicated between a generator G 640 and a discriminator D 670, as part of training in a conditional GAN arrangement. As shown, the generator G 650 receives a set of training data which includes an anatomical mapping image 644A in addition to an input dose image 642. As previously discussed, the generator G 650 is adapted to generate a simulated (e.g., estimated, artificial, etc.) output dose image 662 from this input dose image. The discriminator D 670, however, is adapted to also receive an instance of the same anatomical area information 644B as the condition when operating the discriminator D 670, with this condition thus assisting the discriminator D 670 in producing the determination value 672. The discriminator D 670 and generator G 650 then adjust training weights 665 as a result of this operation flow 630 to improve each others' results. FIG. 6B shows the configuration of the combined networks for training, and FIG. 6C shows the trained generator network operating alone to estimate the dose for an image input.

The preceding examples provide an example of how a GAN or conditional GAN may be trained based on an anatomical mapping image and an output dose image, specifically from image data in 2D image slices. It will be understood that the GAN or conditional GAN may process other forms of image data (e.g., 3D, or other multi-dimensional images). Other forms of non-image data representing the anatomical area and other treatment or diagnostic space may also be used in training or prediction use cases. Further, although only grayscale (including black and white) images are depicted by the accompanying drawings, it will be understood that color images may be generated and/or processed by the GAN, as discussed in the examples below.

Thus, data preparation for training requires an anatomy representation and a dose representation. In an example, the original data used for training consists of pairs of CT image sets and corresponding 3D dose distributions. Because most current CNN platforms provide algorithms that are best suited to 2D images, the CT and dose data may be registered and resampled to a common coordinate frame to produce pairs of anatomy-derived images and dose sections.

Figure 7:
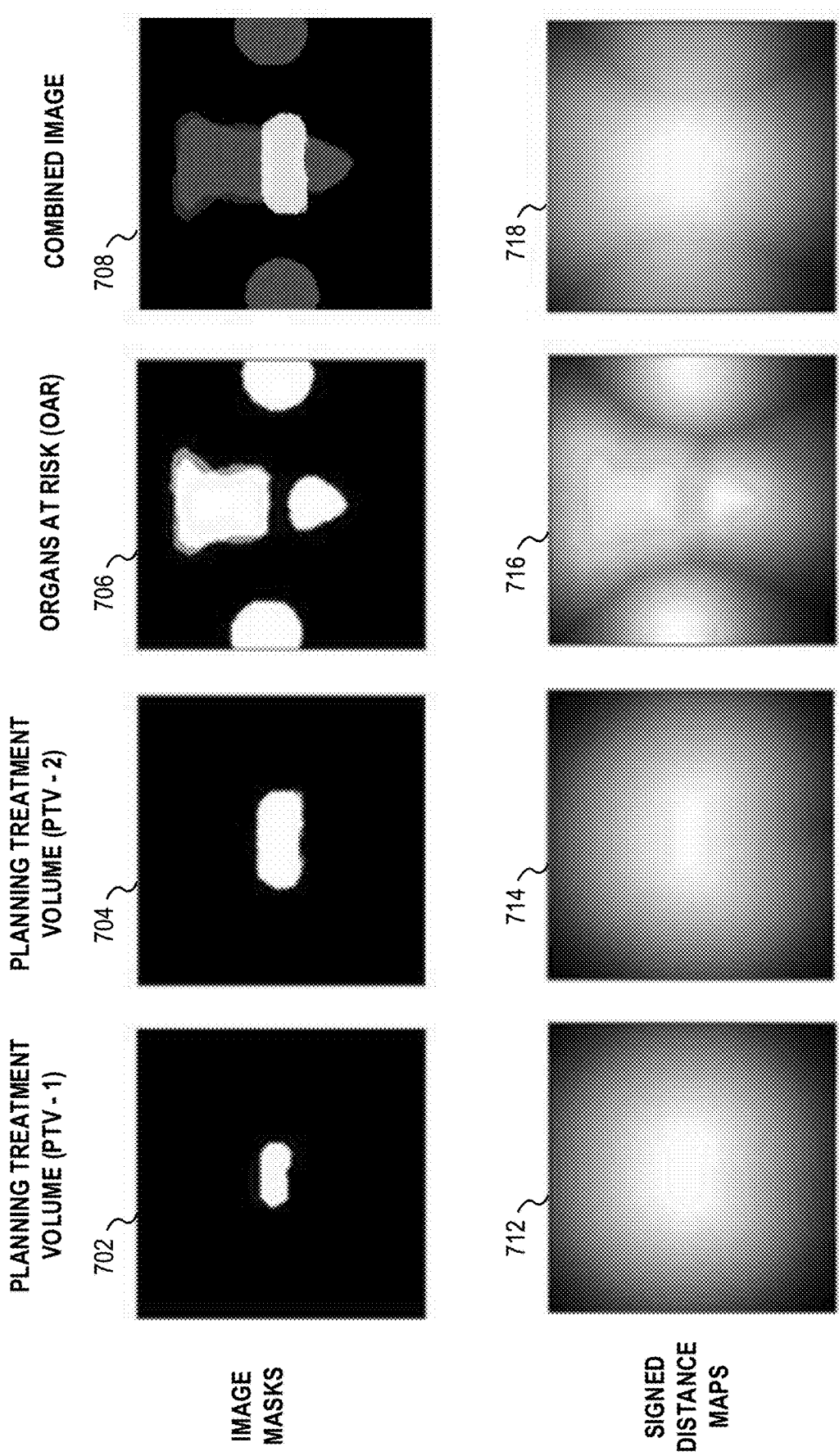
FIG. 7 illustrates variations of anatomical area information and input images used in connection with training and generating a treatment dose model.

FIG. 7 illustrates variations of anatomical area information and input images used in connection with training and generating a treatment dose model. In FIG. 7, two anatomy representations are shown. First, binary image masks 702, 704 of the planning treatment volume targets (PTV-1, PTV-2) and the collective OARs 706 are shown in the top row. Second, signed distance maps 712, 714, 716, derived from these images, are shown in the bottom row that represent the distance from any point in space to the closest object boundary.

In an example, an additional constraint imposed by the processing CNN involves combining the three anatomies into a single data representation (e.g., combined image 708 based on image masks 702, 704, 706; or combined image 718 based on signed distance maps 712, 714, 716). In the depicted example of FIG. 8, this combination of the three anatomical areas (e.g., 702, 704, 706; or 712, 714, 716) may be represented by respective values in a single image channel (e.g. different grayscale values in a grayscale image). In another example, this combination of the three anatomical areas (e.g., 702, 704, 706; or 712, 714, 716) may be represented by corresponding channels (e.g., three channels) of a single 8-bit RGB image (708, 718, depicted in FIG. 8 in grayscale). Other anatomy representations are possible including, for example, combinations of the binary masks with the original CT images, or other derivations or combinations.

FIG. 8 illustrates variations of pairs of anatomical area information and output dose representations provided in a treatment dose model. As shown, a resampled 3D dose distribution may sliced onto planes at the same coordinates as the anatomy images, as the resampled dose can be interpolated using nearest neighbor or linear interpolation. FIG. 8 illustrates four combinations of anatomy (binary map image 802 with linear interpolation 804 or nearest neighbor 814; and signed distance map image 812 with linear interpolation 824 or nearest neighbor 834).

In an example, an estimate of a radiotherapy dose distribution may be generated as a result of training a cGAN network and output as a DVH representation. The network may carry out the two-player minimax game described by equation (18), such as by using a specific implementation of the cGAN algorithm (e.g., as implemented in TensorFlow). A result of radiotherapy dose estimation may be generated from a cGAN network at select time points during training, such as during different epochs. Other forms of visualizations, comparisons, or validations of training or predicted results may also be utilized in connection with a GAN-trained generative model.

In still further examples, optimizations may be used to perform a comparison of ground truth and cGAN DVHs at select time points during network training. For instance, DVHs may be generated and evaluated to verify the avoidance of the OARs. For instance, for prostate cancer therapy, the two largest nearby organs are the bladder and the rectum. The DVHs for the bladder and rectum for each training time point may be tracked, compared, and visualized (e.g., to determine whether the OAR DVHs for the GAN estimates are not very different from those of the ground truth DVHs).

Figure 9:
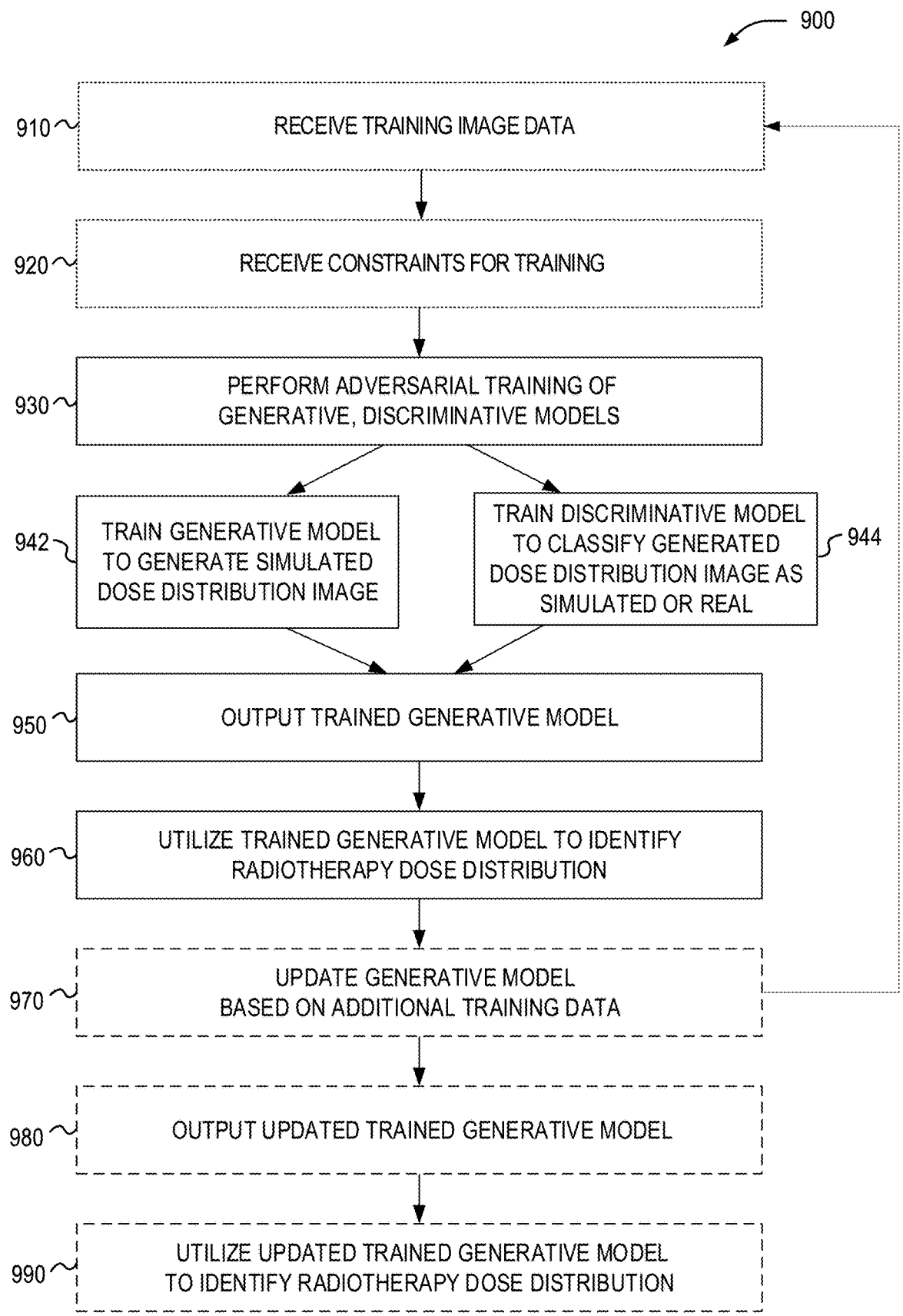
FIG. 9 illustrates a flowchart of exemplary operations for training a generative model adapted for outputting a treatment dose.

FIG. 9 illustrates a process flowchart 900 of exemplary operations for training a generative model adapted for outputting a treatment dose. The process flow 900 is illustrated from the perspective of a radiotherapy treatment processing system which trains and utilizes a generative model, using a GAN as discussed in the preceding examples. However, corresponding operations may be performed by other devices or systems (including in offline training or verification settings separate from a particular radiation therapy treatment workflow or medical treatment).

As shown, a first phase of the flowchart workflow begins with precondition operations (910, 920) to establish the parameters of training and model operations. The flowchart 900 begins with operations to receive (e.g., obtain, extract, identify) training image data (operation 910) and constraints or conditions for training (operation 920). In an example, this training image data may comprise image data from a plurality of human subjects, relating to a particular condition, anatomical feature, or anatomical area. Also in an example, the constraints or conditions may relate to treatment device, patient, or medical treatment considerations.

The second phase of the flowchart 900 continues with training operations, including adversarial training of generative and discriminative models in a generative adversarial network (operation 930). In an example, the adversarial training includes training the generative model to generate a simulated radiotherapy dose distribution image from an input anatomical area image (operation 942) and training the discriminative model to classify a generated radiotherapy dose distribution image as simulated or real training data (operation 944). Also in this adversarial training, the output of the generative model is used for training the discriminative model, and the output of the discriminative model is used for training the generative model. In various examples, the generative model and the discriminative model comprise respective convolutional neural networks (e.g., as discussed with reference to FIG. 3 above). In further examples, the generative adversarial network is a conditional generative adversarial network (e.g., as discussed with reference to FIGS. 6A to 6C above).

The flowchart 900 continues with the output of the generative model for use in generating radiotherapy treatment dose information (operation 950), as the generative model is adapted to identify a radiotherapy dose data for a radiotherapy treatment of a human subject based on input anatomical data that corresponds to a mapping of an anatomical structure for the radiotherapy treatment. The trained generative model is utilized in this manner to identify a radiotherapy dose distribution (operation 960), such as is further discussed below in flowchart 1000 depicted in FIG. 10.

The flowchart 900 concludes with a final phase to implement updates to the generative model, including updating the generative model based on additional training data (operation 970) and outputting the updated trained generative model (operation 980). In various examples, the updating may be produced in connection with the receipt of additional training image data and constraints (e.g., in a manner similar to operations 910, 920), or the performance of additional adversarial training (e.g., in a manner similar to operations 930, 942, 944). In further examples, the generative model may be specifically updated based on approval, changes, or use of the radiotherapy dose data (e.g., resulting from modification, verification, or changes to the dose data by a medical professional). The flowchart concludes with the use of the updated trained generative model (operation 990), such as may be performed in uses of the updated generative model for subsequent radiotherapy treatments.

Figure 10:
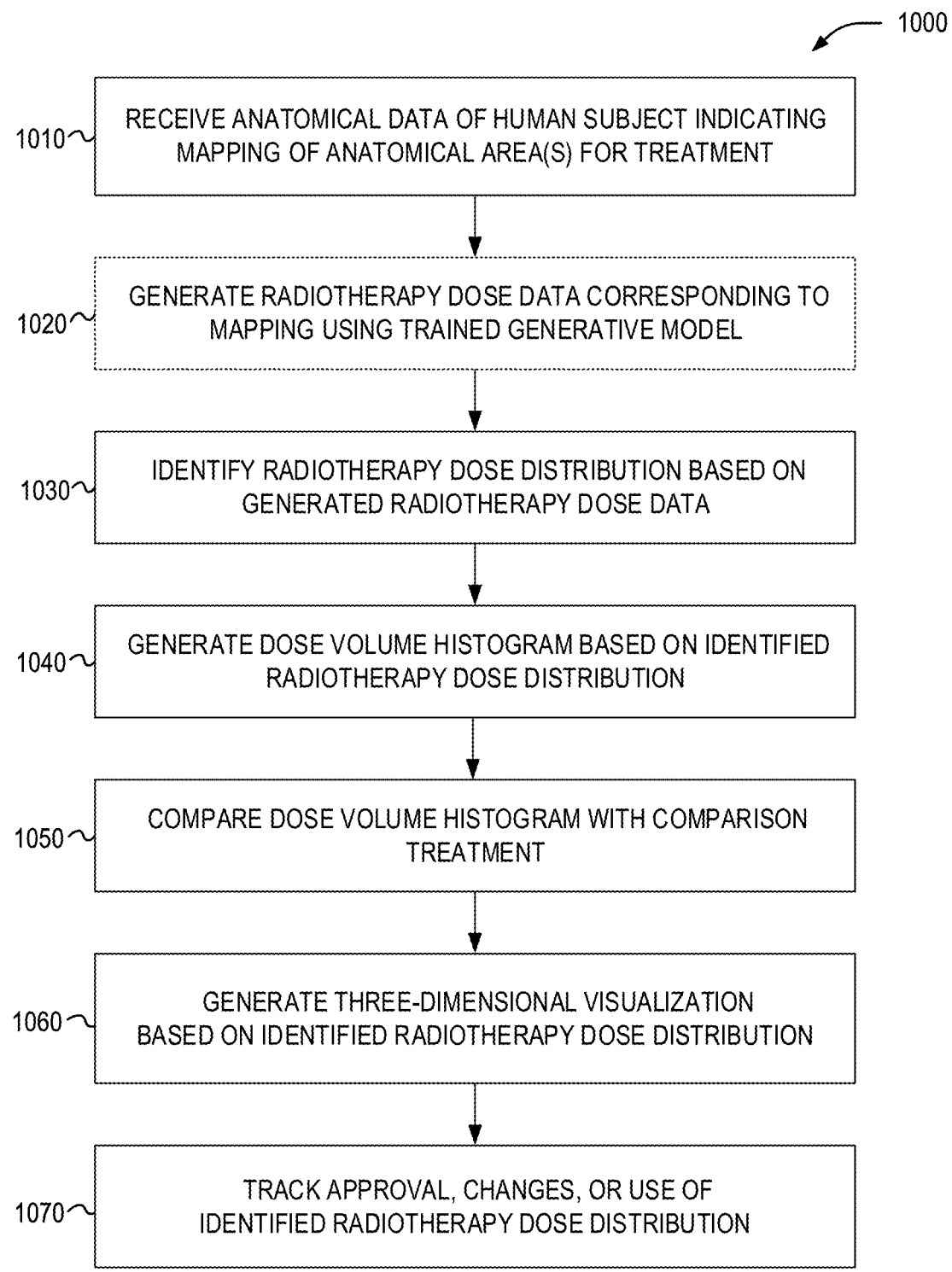
FIG. 10 illustrates a flowchart of exemplary operations for utilizing a generative model adapted for outputting for a treatment dose.

FIG. 10 illustrates a process flowchart 1000 of exemplary operations for performing deep learning assisted dose estimation and comparison with the clinical plan dose with use of machine learning regression. The process flowchart 1000 is also illustrated from the perspective of a radiation treatment processing system which utilizes a machine learning dose estimator, using the GAN-trained generative model (e.g., trained using the process in flowchart 900). However, corresponding operations may be performed or invoked by other devices or systems (including in a variety of client-side systems providing medical diagnostic and evaluative functions).

The flowchart 1000 begins with the receipt and processing of anatomical data of a human subject, which indicates a mapping of one or more anatomical areas for treatment (operation 1010). In an example, the anatomical data is represented in image data, and the mapping of the anatomical area comprises a plurality of image masks corresponding to at least one area identified to receive the radiotherapy treatment and at least one area identified to avoid the radiotherapy treatment. In a further example, the anatomical data is identified from a three-dimensional image set of the anatomical area of the human subject, or the anatomical data comprises three-dimensional voxel data of the anatomical area derived from at least one image of the human subject captured by at least one imaging modality, and the plurality of image masks correspond to respective segments indicating at least one region identified to receive the radiotherapy treatment and at least one organ at risk identified to avoid the radiotherapy treatment. In other examples, the anatomical data comprises an image including at least one binary mask or at least one signed distance map, or the anatomical data comprises coordinates for radiotherapy treatment within a coordinate space of the anatomical area. In a specific example, the image comprises a Digital Imaging and Communications in Medicine (DICOM) format image produced from an imaging modality.

The flowchart 1000 continues with the generation of radiotherapy dose data corresponding to a mapping of the one or more anatomical areas, with such generation occurring using a trained generative model. In an example, the generative model is trained in a generative adversarial network, and the generative model is further trained to process the anatomical data as an input and provide the radiotherapy dose data as an output. In a further example, the generative adversarial network is configured to train the generative model using a discriminative model, and values applied by the generative model and the discriminative model are established using adversarial training between the discriminative model and the generative model. In a further example, the generative model and the discriminative model comprise respective convolutional neural networks, as discussed above. In still a further example, the adversarial training may occur with the techniques discussed with reference to FIG. 9. In a further example, the generative model is identified from among a plurality of models trained by the generative adversarial network, and the generative model is identified based on the anatomical area or a type of the radiotherapy treatment.

In specific examples, the input image is a two-dimensional image that comprises respective areas representing the at least one treatment area and at least one treatment exclusion area using respective image channels or respective grayscale values in an image channel, and the simulated radiotherapy dose distribution image is a two-dimensional image that comprises respective areas representing dose values using respective image color channels or respective values in an image channel. In further examples, the generative model is trained to receive the input image as a RGB image color image comprising image masks indicating the at least one treatment area and the at least one treatment exclusion area with at least two color image channels, and the generative model is trained to produce the simulated radiotherapy dose distribution image as a grayscale image. Also in further examples, the radiotherapy dose data comprises an image produced from linear interpolation or nearest neighbor interpolation of archived dose data at a lower resolution; or, the radiotherapy dose data comprises an indication of an amount of radiotherapy treatment at the coordinates within the coordinate space of the anatomical area.

As discussed above with reference to FIGS. 6 and 9, the generative adversarial network may be a conditional generative adversarial network comprising the generative model and a discriminative model, and the predicted values provided from the generative model are conditioned on the imaging data captured from the human subject. For instance, the generative model and the discriminative model may be conditioned on pre-classified anatomical structure data during training, where the pre-classified anatomical structure data corresponds to the anatomical area for radiotherapy treatment. Also for instance, the generative model and the discriminative model of the conditional generative adversarial network are further conditioned on at least one constraint associated with the radiotherapy dose distribution. As an example, the constraint may be tied to or derived from radiotherapy treatment constraints, anatomy, treatment machine limitations, or associated parameters and features. In still another example, the generative model is identified from among a plurality of models trained by the generative adversarial network, and the generative model is identified based on the anatomical area or a type of the radiotherapy treatment.

The flowchart 1000 continues with operations to identify the radiotherapy dose distribution for the radiotherapy treatment of the human subject based on the radiotherapy dose data (operation 1030). As indicated previously, the generative model will be trained to generate the radiotherapy dose data for a particular condition or anatomical feature based on data (e.g., three-dimensional image data) obtained from a plurality of human subjects.

The identification of the radiotherapy dose distribution may be followed with operations that generate at least one dose volume histogram of the radiotherapy dose distribution (operation 1040) identified for the radiotherapy treatment of the human subject, with use of one or more dose volume histograms that indicate values for at least one planning treatment volume or at least one organ at risk; and comparing the dose volume histogram of the radiotherapy dose distribution with a dose volume histogram generated for another radiotherapy dose distribution (operation 1050), with such distribution identified for a radiotherapy treatment corresponding to the anatomical area. This may be followed by features that generate a three-dimensional visualization of the anatomical area (operation 1060), with the three-dimensional visualization indicating the radiotherapy dose distribution identified for the radiotherapy treatment of the human subject.

The flowchart 1000 concludes with tracking features (operation 1070) that involve updating the generative model based on approval, changes, or use of the radiotherapy dose data, generating, using the updated generative model, an updated radiotherapy dose distribution for the human subject. Further variation for additional feedback, monitoring, and utilization of the radiotherapy dose data may be integrated into other treatment or evaluative workflows.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 202, perform or implement the training or prediction operations from model 300, operate the trained generator model 460, perform or implement the data flows 500, 550, 600, 630, 680, perform or implement the operations of the flowcharts 900, 1000, or perform any one or more of the other methodologies discussed herein (e.g., as part of treatment processing logic 120 and the workflows 130, 140). In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine readable medium. While the machine-readable medium may have been described in various examples with reference to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present invention also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and example parameters, functions, and implementations described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A computer implemented method for generating a radiotherapy dose distribution using a trained model, the method comprising:

receiving anatomical data of a human subject, the anatomical data indicating a mapping of an anatomical area for radiotherapy treatment of the human subject;

generating, using a generative model, radiotherapy dose data corresponding to the mapping, the generative model being trained in a generative adversarial network, wherein the generative model is further trained to process the anatomical data as an input and provide the radiotherapy dose data as an output;

converting the radiotherapy dose data from the generative model into a radiotherapy dose distribution, wherein the radiotherapy dose data from the generative model identifies radiotherapy dosage to be delivered to the anatomical area; and outputting the radiotherapy dose distribution for use in the radiotherapy treatment of the human subject.

2. The method of claim 1, wherein the generative adversarial network is configured to train the generative model using a discriminative model, wherein values applied by the generative model and the discriminative model are established using adversarial training between the discriminative model and the generative model, and wherein the generative model and the discriminative model comprise respective convolutional neural networks; and wherein the radiotherapy dose data from the generative model identifies the radiotherapy dosage to be delivered to the anatomical area according to a treatment plan, and wherein the use of the radiotherapy dose distribution includes use of the treatment plan to perform the radiotherapy treatment.

3. The method of claim 2, wherein the adversarial training comprises training the generative model to generate a simulated radiotherapy dose distribution image from an input image that indicates at least one treatment area, and training the discriminative model to classify an input radiotherapy dose distribution image as simulated or real training data, and wherein output of the generative model is used for training the discriminative model and output of the discriminative model is used for training the generative model.

4. The method of claim 3, wherein the input image and the simulated radiotherapy dose distribution image comprise respective three-dimensional images.

5. The method of claim 3, wherein the input image is a two-dimensional image that comprises respective areas which depict the at least one treatment area and at least one treatment exclusion area using respective image channels or respective grayscale values in an image channel, and wherein the simulated radiotherapy dose distribution image is a two-dimensional image that comprises respective areas which depict dose values using respective image color channels or respective values in an image channel.

6. The method of claim 5, wherein the generative model is trained to receive the input image as a RGB color image comprising image masks indicating the at least one treatment area and the at least one treatment exclusion area with at least two image color channels, and wherein the generative model is trained to produce the simulated radiotherapy dose distribution image as a grayscale image.

7. The method of claim 3, wherein the input image comprises a Digital Imaging and Communications in Medicine (DICOM) format image produced from an imaging modality.

8. The method of claim 1, wherein the anatomical data is provided by image data, and wherein the mapping of the anatomical area comprises a plurality of image masks corresponding to at least one area identified to receive the radiotherapy treatment and at least one area identified to avoid the radiotherapy treatment.

9. The method of claim 8,
wherein the anatomical data comprises three-dimensional voxel data of the anatomical area derived from at least one image of the human subject captured by at least one imaging modality, and
wherein the plurality of image masks correspond to respective segments indicating at least one region identified to receive the radiotherapy treatment and at least one organ at risk identified to avoid the radiotherapy treatment.

10. The method of claim 1,
wherein the anatomical data comprises an image including at least one binary mask or at least one signed distance map, and
wherein the radiotherapy dose data comprises an image produced from linear interpolation or nearest neighbor interpolation of archived dose data at a lower resolution.

11. The method of claim 1,
wherein the anatomical data comprises coordinates for radiotherapy treatment within a coordinate space of the anatomical area, and
wherein the radiotherapy dose data comprises an indication of an amount of radiotherapy treatment at the coordinates within the coordinate space of the anatomical area.

12. The method of claim 1,
wherein the generative model is identified from among a plurality of models trained by the generative adversarial network, and
wherein the generative model is identified based on the anatomical area or a type of the radiotherapy treatment.

13. The method of claim 1,
wherein the anatomical data comprises imaging data captured from the human subject, wherein the generative adversarial network is a conditional generative adversarial network comprising the generative model and a discriminative model, and
wherein predicted values provided from the generative model are conditioned on the imaging data captured from the human subject.

14. The method of claim 13, wherein the generative model and the discriminative model are conditioned on pre-classified anatomical structure data during the training in a generative adversarial network, and
wherein the pre-classified anatomical structure data corresponds to the anatomical area for radiotherapy treatment.

15. The method of claim 14, wherein the generative model and the discriminative model are further conditioned on at least one target or critical structure constraint associated with the radiotherapy dose distribution.

16. The method of claim 15,
wherein the anatomical data is identified from a three-dimensional image set of the anatomical area of the human subject, and
wherein the generative model is trained to generate the radiotherapy dose data for a particular condition or anatomical feature based on three-dimensional image data obtained from a plurality of human subjects.

17. The method of claim 1, wherein the generative model is further trained for subsequent events of the radiotherapy treatment of the human subject, with operations comprising:
updating the generative model based on approval, changes, or use of the radiotherapy dose data; and
outputting, using the updated generative model, updated radiotherapy dose data, wherein the updated radiotherapy dose data from the updated generative model is converted into the radiotherapy dose distribution for use in the radiotherapy treatment of the human subject.

18. The method of claim 1, further comprising:
generating at least one dose volume histogram of the radiotherapy dose distribution identified for the radiotherapy treatment of the human subject, wherein the at least one dose volume histogram indicates values for at least one planning treatment volume or at least one organ at risk; and
comparing the at least one dose volume histogram of the radiotherapy dose distribution with at least one dose volume histogram generated for another radiotherapy dose distribution identified for a radiotherapy treatment corresponding to the anatomical area.

19. The method of claim 1, further comprising:
generating a three-dimensional visualization of the anatomical area, the three-dimensional visualization indicating the radiotherapy dose distribution identified for the radiotherapy treatment of the human subject.

20. A computer-implemented method for producing a trained model for generating a radiotherapy dose distribution using a generative adversarial network, the method comprising:
establishing values of a generative model and a discriminative model of the generative adversarial network using adversarial training, the adversarial training comprising:
training the generative model to generate a simulated radiotherapy dose distribution image from an input image; and
training the discriminative model to classify an input radiotherapy dose distribution image as simulated or real training data;
wherein output of the generative model is used for training the discriminative model, and wherein output of the discriminative model is used for training the generative model; and
outputting the generative model for use in generating radiotherapy treatment dose information, wherein the generative model is adapted for outputting radiotherapy dose data that identifies radiotherapy dosage to be delivered in a radiotherapy treatment of a human subject, and wherein the radiotherapy treatment is to be delivered based on input anatomical data that corresponds to a mapping of an anatomical structure for the radiotherapy treatment.

21. The method of claim 20,
wherein the generative model and the discriminative model comprise respective convolutional neural networks,
wherein the input image comprises respective areas which depict at least one treatment area and at least one treatment exclusion area using respective image color channels or respective grayscale values in an image channel, and wherein the simulated radiotherapy dose distribution image comprises respective areas which depict dose values using respective image color channels or respective values in an image channel.

22. The method of claim 20,
wherein the generative adversarial network is a conditional generative adversarial network, and
wherein the generative model and the discriminative model are conditioned using pre-defined anatomical structure data during the training of the generative model and during the training of the discriminative model respectively, the pre-defined anatomical structure data corresponding to an area of anatomy relating to the radiotherapy treatment.

23. The method of claim 20, wherein the mapping of the anatomical structure comprises a plurality of image masks indicating at least one area identified for radiotherapy treatment and at least one area identified to avoid the radiotherapy treatment.

24. The method of claim 20,
wherein the generative model is trained to generate the radiotherapy dose data for a particular condition or anatomical feature based on image data from a plurality of human subjects,
wherein the anatomical data comprises respective anatomical images from the plurality of human subjects including at least one binary image mask or signed distance map, and
wherein the radiotherapy dose data comprises respective images corresponding to the anatomical images, the radiotherapy dose data produced from linear interpolation or nearest neighbor interpolation.

25. The method of claim 20, wherein the generative model is trained on a plurality of anatomical areas for respective radiotherapy treatments.

26. A system for generating a radiotherapy dose distribution using a trained model, the system comprising:
processing circuitry comprising at least one processor; and
a storage medium comprising instructions, which when executed by the at least one processor, cause the at least one processor to:
process anatomical data of a human subject, the anatomical data indicating a mapping of an anatomical area for radiotherapy treatment of the human subject;
generate, using a generative model, radiotherapy dose data corresponding to the mapping, the generative model being trained in a generative adversarial network, wherein the generative model is further trained to process the anatomical data as an input and provide the radiotherapy dose data as an output;
convert the radiotherapy dose data from the generative model into a radiotherapy dose distribution, wherein the radiotherapy dose data from the generative model identifies radiotherapy dosage to be delivered to the anatomical area; and
output the radiotherapy dose distribution for use in the radiotherapy treatment of the human subject.

27. The system of claim 26,
wherein the generative adversarial network is configured to train the generative model using a discriminative model, wherein values applied by the generative model and the discriminative model are established using adversarial training between the discriminative model and the generative model, and wherein the generative model and the discriminative model comprise respective convolutional neural networks; and
wherein the radiotherapy dose data from the generative model identifies the radiotherapy dosage to be delivered to the anatomical area according to a treatment plan, and wherein the use of the radiotherapy dose distribution includes use of the treatment plan to perform the radiotherapy treatment.

28. The system of claim 27,
wherein the adversarial training comprises training of the generative model to generate a simulated radiotherapy dose distribution image from an input image that indicates at least one treatment area, and training of the discriminative model to classify an input radiotherapy dose distribution image as simulated or real training data, and
wherein output of the generative model is used for training the discriminative model and output of the discriminative model is used for training the generative model.

29. The system of claim 28, wherein the input image and the simulated radiotherapy dose distribution image comprise respective three-dimensional images.

30. The system of claim 28,
wherein the input image is a two-dimensional image that comprises respective areas which depict the at least one treatment area and at least one treatment exclusion area using respective image color channels or respective grayscale values in an image channel, and
wherein the simulated radiotherapy dose distribution image is a two-dimensional image that comprises respective areas which depict dose values using respective image color channels or respective values in an image channel.

31. The system of claim 30,
wherein the generative model is trained to receive the input image as a RGB color image comprising image masks indicating the at least one treatment area and the at least one treatment exclusion area with at least two image color channels, and
wherein the generative model is trained to produce the simulated radiotherapy dose distribution image as a grayscale image.

32. The system of claim 28, wherein the input image comprises a Digital Imaging and Communications in Medicine (DICOM) format image produced from an imaging modality.

33. The system of claim 28, wherein the anatomical data is provided by image data, and wherein the mapping of the anatomical area comprises a plurality of image masks corresponding to at least one area identified to receive the radiotherapy treatment and at least one area identified to avoid the radiotherapy treatment.

34. The system of claim 33,
wherein the anatomical data comprises three-dimensional voxel data of the anatomical area derived from at least one image of the human subject captured by at least one imaging modality, and
wherein the plurality of image masks correspond to respective segments indicating at least one region identified to receive the radiotherapy treatment and at least one organ at risk identified to avoid the radiotherapy treatment.

35. The system of claim 26,
wherein the anatomical data comprises an image including at least one binary mask or at least one signed distance map, and wherein the radiotherapy dose data comprises an image produced from linear interpolation or nearest neighbor interpolation of archived dose data at a lower resolution.

36. The system of claim 26,
wherein the anatomical data comprises coordinates for radiotherapy treatment within a coordinate space of the anatomical area, and
wherein the radiotherapy dose data comprises an indication of an amount of radiotherapy treatment at the coordinates within the coordinate space of the anatomical area.

37. The system of claim 26,
wherein the generative model is identified from among a plurality of models trained by the generative adversarial network, and
wherein the generative model is identified based on the anatomical area or a type of the radiotherapy treatment.

38. The system of claim 26,
wherein the anatomical data comprises imaging data captured from the human subject, wherein the generative adversarial network is a conditional generative adversarial network comprising the generative model and a discriminative model, and
wherein predicted values provided from the generative model are conditioned on the imaging data captured from the human subject.

39. The system of claim 38, wherein the generative model and the discriminative model are conditioned on pre-classified anatomical structure data during the training in a generative adversarial network, and
wherein the pre-classified anatomical structure data corresponds to the anatomical area for radiotherapy treatment.

40. The system of claim 39, wherein the generative model and the discriminative model are further conditioned on at least one target or critical structure constraint associated with the radiotherapy dose distribution.

41. The system of claim 40,
wherein the anatomical data is identified from a three-dimensional image set of the anatomical area of the human subject, and
wherein the generative model is trained to generate the radiotherapy dose data for a particular condition or anatomical feature based on three-dimensional image data obtained from a plurality of human subjects.

* * * * *